(12) United States Patent
Zeilhofer et al.

(10) Patent No.: US 10,786,513 B2
(45) Date of Patent: Sep. 29, 2020

(54) USE OF GABA$_A$ RECEPTOR MODULATORS FOR TREATMENT OF ITCH

(71) Applicant: UNIVERSITÄT ZÜRICH, Zürich (CH)

(72) Inventors: Hanns Ulrich Zeilhofer, Zürich (CH); William Ralvenius, Somerville, MA (US)

(73) Assignee: UNIVERSITAT ZURICH, Zurich (CH)

(*) Notice: Subject to any disclaimer, the term of this patent is extended or adjusted under 35 U.S.C. 154(b) by 0 days.

(21) Appl. No.: 16/045,193

(22) Filed: Jul. 25, 2018

(65) Prior Publication Data

US 2019/0134057 A1   May 9, 2019

Related U.S. Application Data

(63) Continuation of application No. PCT/EP2017/051866, filed on Jan. 27, 2017.

(30) Foreign Application Priority Data

Jan. 27, 2016 (EP) .................................. 16153035
Jul. 11, 2016 (EP) .................................. 16178824

(51) Int. Cl.

| A61K 31/5517 | (2006.01) |
|---|---|
| A61K 31/53 | (2006.01) |
| A61K 31/519 | (2006.01) |
| A61K 31/437 | (2006.01) |
| A61K 31/4184 | (2006.01) |
| A61K 31/5025 | (2006.01) |
| A61K 31/5513 | (2006.01) |
| A61P 17/04 | (2006.01) |
| A61K 31/4188 | (2006.01) |

(52) U.S. Cl.
CPC ...... *A61K 31/5517* (2013.01); *A61K 31/4184* (2013.01); *A61K 31/4188* (2013.01); *A61K 31/437* (2013.01); *A61K 31/5025* (2013.01); *A61K 31/519* (2013.01); *A61K 31/53* (2013.01); *A61K 31/5513* (2013.01); *A61P 17/04* (2018.01)

(58) Field of Classification Search
CPC ............. A61K 34/437; A61K 31/5025; A61K 31/519; A61K 31/5513; A61K 31/53; A61K 31/4188; A61K 31/4148; A61K 31/5517; A61P 17/04

See application file for complete search history.

(56) References Cited

U.S. PATENT DOCUMENTS

| 6,572,848 B1 | 6/2003 | Breton et al. |
|---|---|---|
| 6,617,326 B2 | 9/2003 | Carling et al. |
| 6,630,471 B1 | 10/2003 | Carling et al. |
| 6,696,444 B2 | 2/2004 | Carling et al. |
| 6,936,608 B2 | 8/2005 | Bettati et al. |
| 7,005,431 B2 | 2/2006 | Bettati et al. |
| 7,119,196 B2 | 10/2006 | Cook et al. |
| 8,809,541 B2 | 8/2014 | Gwak et al. |
| 8,835,424 B2 | 9/2014 | Cook et al. |
| 9,199,965 B2 * | 12/2015 | Kim ............. C07D 401/10 |
| 1,024,526 A1 | 4/2019 | Weng et al. |
| 2005/0245517 A1 | 11/2005 | Skolnick et al. |
| 2011/0082147 A1 | 4/2011 | Harbeson et al. |
| 2011/0195950 A1 | 8/2011 | Hintermann et al. |
| 2016/0199373 A1 | 7/2016 | Erickson et al. |
| 2019/0083493 A1 | 3/2019 | Erickson et al. |

FOREIGN PATENT DOCUMENTS

| EP | 2960234 A1 | 12/2015 |
|---|---|---|
| JP | 2004170323 A | 6/2004 |
| WO | WO-0047582 A1 | 8/2000 |
| WO | WO-02074773 | 9/2002 |
| WO | WO-2005030773 A1 | 4/2005 |
| WO | 2006061428 * | 6/2006 |
| WO | WO-2006061428 A2 | 6/2006 |
| WO | 2008015271 * | 2/2008 |
| WO | WO-2008015271 A1 | 2/2008 |
| WO | WO-2008064157 A1 | 5/2008 |
| WO | WO-2009143211 A2 | 11/2009 |
| WO | WO-2010124108 A1 | 10/2010 |
| WO | WO-2011011712 A1 | 1/2011 |
| WO | 2012026765 * | 3/2012 |
| WO | WO-2015072853 A1 | 5/2015 |
| WO | WO-2015086503 A1 | 6/2015 |

(Continued)

OTHER PUBLICATIONS

Zeilhofer et al., Restoring the spinal pain gate: GABAA receptors as targets for novel analgesics, Institute of Pharmacology and Toxicology, University of Zurich, Zurich, Switz. Advances in Pharmacology (San Diego, CA, United States) (2015), 73(Diversity and Functions of GABA. (Year: 2015).*

Muller Herde et al., GABAA receptor subtypes in the mouse brain: Regional mapping and diazepam receptor occupancy by in vivo [18F] flumazenil PET; Inst. Pharm Sci, Department of Chemistry and Applied Biosciences (D-CHAB), ETH Zurich, Zurich, CH-8093, Switz. m NeuroImage (2017), 150, 279-291. (Year: 2017).*

Edmund Foster et al., Targeted Ablation, Silencing, and Activation Establish Glycinergic Dorsal Horn Neurons as Key components of Spinal Gate for Pain and Itch. Neuron (2015), 85(6), 1289-1304. (Year: 2015).*

(Continued)

*Primary Examiner* — Mark L Shibuya
*Assistant Examiner* — Ebenezer O Sackey
(74) *Attorney, Agent, or Firm* — Wilson Sonsini Goodrich & Rosati

(57) ABSTRACT

A compound for use in the treatment of itch is provided, wherein the compound comprises the general formula (1a), general formula (1b) or general formula (1c). The compounds of the invention are positive allosteric α2 and/or α3 GABA$_A$ receptor modulators.

7 Claims, 20 Drawing Sheets

(56) References Cited

FOREIGN PATENT DOCUMENTS

Figure 1A:
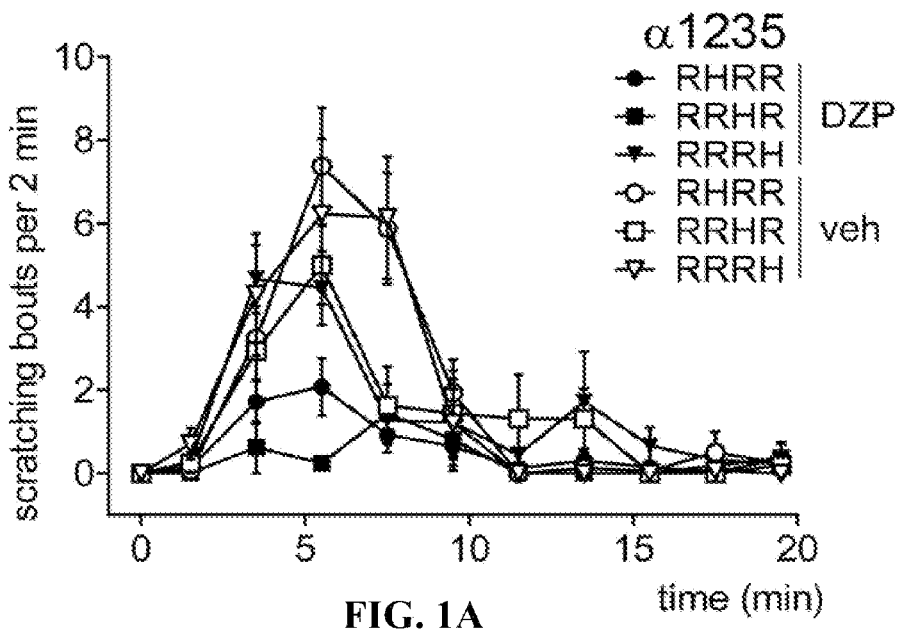

| WO | WO-2016154031 A1 | 9/2016 |
|---|---|---|
| WO | WO-2017129801 A1 | 8/2017 |

OTHER PUBLICATIONS

R. Nigam et al., 302 Archives of Dermatological Research, 507-515 (2010) (Year: 2010).*

Akimoto, et al., SCH23390, a dopamine D1 receptor antagonist, suppressed scratching behavior induced by compound 48/80 in mice. Eur J Pharmacol. Nov. 16, 2011;670(1):162-7.

Amrutkar, D., et al., SAN711, a novel GABAA α3 Receptor subtype preferring positive allosteric modulator for the treatment of neuropathic pain and pruritus. Presentation poster. Saniona, IASP (2018), Boston,USA.

Besson, et al., GABAergic modulation in central sensitization in humans: a randomized placebo-controlled pharmacokinetic-pharmacodynamic study comparing clobazam with clonazepam in healthy volunteers. Pain. Mar. 2015;156(3):397-404.

Beyer, et al., Blockage of substance P-induced scratching behavior in rats by the intrathecal administration of inhibitory amino acid agonists. Pharmacol Biochem Behav. Nov. 1989;34(3):491-5.

Carter, et al., Characterization of the anticonvulsant properties of ganaxolone (CCD 1042; 3alpha-hydroxy-3beta-methyl-5alpha-pregnan-20-one), a selective, high-affinity, steroid modulator of the gamma-aminobutyric acid(A) receptor. J Pharmacol Exp Ther. Mar. 1997;280(3):1284-95.

De Lucas, et al., GABAA α5 subunit-containing receptors do not contribute to reversal of inflammatory-induced spinal sensitization as indicated by the unique selectivity profile of the GABAA receptor allosteric modulator NS16085. Biochem Pharmacol. Feb. 1, 2015;93(3):370-9.

Dias, et al., Evidence for a Significant Role of α3-Containing GABAA Receptors in Mediating the Anxiolytic Effects of Benzodiazepines. Journal of Neuroscience Nov. 16, 2005, 25 (46) 10682-10688; DOI: https://doi.org/10.1523/JNEUROSCI.

Dugue, et al., Electrical coupling mediates tunable low-frequency oscillations and resonance in the cerebellar Golgi cell network. Neuron, Jan. 15, 2009; 61(1):126-39.

Han, et al., A subpopulation of nociceptors specifically linked to itch. Nat Neurosci. Feb. 2013;16(2):174-82. doi: 10.1038/nn.3289. Epub Dec. 23, 2012.

Jensen, et al., Clobazam and Its Active Metabolite N-desmethylclobazam Display Significantly Greater Affinities for α2-versus α1-GABAA-Receptor Complexes. PLOS ONE, Feb. 12, 2014; 9(2):e88456.

Kido-Nakahara, et al., Neural peptidase endothelin-converting enzyme 1 regulates endothelin 1-induced pruritus. The journal of clinical investigation, Jun. 2014; 124(6): 2683-2695.

Knabl, et al., Genuine antihyperalgesia by systemic diazepam revealed by experiments in GABAA receptor point-mutated mice. Pain. Feb. 2009;141(3):233-8. doi: 10.1016/j.pain.2008.10.015. Epub Dec. 16, 2008.

Kohut, et al., Novel discriminative stimulus effects of TPA023B, subtype-selective gamma-aminobutyric-acid(A)/benzodiazepine modulator: comparisons with zolpidem, lorazepam, and TPA023. Pharmacol Biochem Behav. Jul. 2008;90(1):65-73.

Labrakakis, et al., Inhibitory coupling between inhibitory interneurons in the spinal cord dorsal horn. Mol Pain. May 12, 2009; 5: 24.

Long, et al., GABA(A) Receptors in the Central Nucleus of the Amygdala are involved in pain- and itch-related responses. J Pain. Feb. 2016;17(2):181-9.

McKernan, et al., Which GABAA-receptor subtypes really occur in the brain? Trends Neurosci. Apr. 1996;19(4):139-43.

Munro, et al., GABA(A) receptor modulation: potential to deliver novel pain medicinces? European Journal of Pharmacology, Mar. 13, 2013; 716(1-3):17-23.

Munro, et al., Comparison of the novel subtype-selective GABAA receptor-positive allosteric modulator NS11394 [3'-[5-(1-hydroxy-1-methyl-ethyl)-benzoimidazol-1-yl]-biphenyl-2-carbonitrile] with diazepam, zolpidem, bretazenil, and gaboxadol in rat models of inflammatory and neuropathic pain. J Pharmacol Exp Ther. Dec. 2008;327(3):969-81. doi: 10.1124/jpet.108.144568. Epub Sep. 12, 2008.

Nickolls, et al., Pharmacology in translation: the preclinical and early clinical profile of the novel α2/3 functionally selective GABAA receptor positive allosteric modulator PF-06372865. British journal of pharmacology. 175; 2018: 708-725.

Nigam, et al., GABA and GABA(A) receptor expression on immune cells in psoriasis: a pathophysiological role. Arch Dermatol Res. Sep. 2010;302(7):507-15.

Paul, et al., Selective Distribution of GABAA Receptor Subtypes in Mouse Spinal Dorsal Horn Neurons and primary afferents. The Journal of Comparative Neurology, Research in Systems Neuroscience 2012; 520:3895-3911.

Ralvenius, et al., Analgesia and unwanted benzodiazepine effects in point-mutated mice expressing only one benzodiazepine-sensitive GABAA receptor subtype. Nature Communication, Apr. 13, 2015;6:6803.

Ralvenius, et al., Itch suppression in mice and dogs by modulation of spinal α2 and α3GABAA receptors. Nature Communications, 2018; 9:3230, 1-15.

Ross, S.E., et al., Loss of inhibitory interneurons in the dorsal spinal cord and elevated itch in Bhlhb5 mutant mice. Neuron. Mar. 25, 2010;65(6):886-98. doi: 10.1016/j.neuron.2010.02.025.

Rudolph, U. & Mohler, H., GABAA receptor subtypes: Therapeutic potential in Down syndrome, affective disorders, schizophrenia, and autism. Annu Rev Pharmacol Toxicol. 2014;54:483-507.

Russell, et al., Discovery of Imidazo[1,2-b][1,2,4]triazines as GABAA α2/3 Subtype Selective Agonists for the Treatment of Anxiety. J. Med. Chem., 2006, 49 (4), pp. 1235-1238 DOI: 10.1021/jm051200u.

Savic, MM., et al., Novel positive allosteric modulators of GABAA receptors: do subtle differences in activity at alpha1 plus alpha5 versus alpha2 plus alpha3 subunits account for dissimilarities in behavioral effects in rats? Prog Neuropsychopharmacol Biol Psychiatry. Mar. 17, 2010;34(2):376-86.

Seidler, et al., A Cre-loxP-based mouse model for conditional somatic gene expression and knockdown in vivo by using avian retroviral vectors. Proc Natl Acad Sci U S A. Jul. 22, 2008;105(29):10137-42.

Li, et al., Improved Synthesis of Anxiolytic, Anticonvulsant, and Antinociceptive α2/α3-GABA(A)-ergic Receptor Subtype Selective Ligands as Promising Agents to Treat Anxiety, Epilepsy, and Neuropathic Pain. Synthesis 2018, 50, 4124-4132.

PCT/EP2017/051866 International Search Report and Written Opinion dated May 15, 2017.

Sun, Y.G., et al., Cellular basis of itch sensation. Science. Sep. 18, 2009; 325(5947): 1531-1534.

Thomsen, et al., Suppression of spontaneous scratching in hairless rats by sedatives but not by antipruritics. Skin Pharmacol Appl Skin Physiol. Jul.-Aug. 2002;15(4):218-24.

Xu, et al., [An animal model for screening of antiallergic and antipruritic drugs].Yao Xue Xue Bao. 1996;31(6):420-4.

Zeilhofer, et al., GABAergic analgesia: new insights from mutant mice and subtype-selective agonists. Trends Pharmacol Sci. Aug. 2009;30(8):397-402. doi: 10.1016/j.tips.2009.05.007. Epub Jul. 16, 2009.

Atack et al., GABAA Receptor Subtype-Selective Efficacy: TPA023, an α2/α3 Selective Nonsedating Anxiolytic and α5IA, an α5 Selective Cognition Enhancer, CNS Neuroscience & Therapeutics, 2008, vol. 14, pp. 25-35.

Atack et al., Preclinical and clinical pharmacology of TPA023B, a GABAA receptor α2/α3 subtype-selective partial agonist, Journal of Psychopharmacology, 2011, vol. 25(3), pp. 329-344.

Dias et al., Evidence for a Significant Role of α3-Containing GABAA Receptors in Mediating the Anxiolytic Effects of Benzodiazepines, The Journal of Neuroscience, 2005, vol. 25 (46), pp. 10682-10688.

Fischer et al., Contribution of GABAA Receptors Containing α3Subunits to the Therapeutic-Related and Side Effects of Benzodiazepine-Type Drugs in Monkeys, Psychopharmacology (Berl)., 2011, vol. 215 (2), pp. 311-319.

(56) References Cited

OTHER PUBLICATIONS

Froestl et al., GABA receptors, BIOTREND Reviews, Review No. Jul. 1, 2011.
Gauthier et al., Palladium-Catalyzed Regioselective Arylation of Imidazo [1,3-b][1,2,4]triazine: Synthesis of an alpha 2/3-selective GABA Agonist in Journal of Organic Chemistry, 2005, vol. 70, pp. 5938-5945.
Morales et al., Anxiolytic effects of the GABAA receptor partial agonist, L-838,417: Impact of age, test context familiarity, and stress, Pharmacol Biochem Behav., 2013, vol. 139, pp. 31-37.
Shinday et al, Reinforcing Effects of Compounds Lacking Intrinsic Efficacy at a1 Subunit-Containing GABAA Receptor Subtypes in Midazolam- But Not Cocaine-Experienced Rhesus Monkeys, Neuropsychopharmacology, 2013, vol. 38 (6), pp. 1006-1014.
Van Laere et al., In Vivo Characterization and Dynamic Receptor Occupancy Imaging of TPA023B, ana2/a3/a5 Subtype Selective-Aminobutyric Acid—A Partial Agonist, Biol Psychiatry, 2008, vol. 64 (2), pp. 153-161.

\* cited by examiner

Contact dermatitis (oxazolone)

Contact dermatitis (oxazolone)

USE OF GABA$_A$ RECEPTOR MODULATORS FOR TREATMENT OF ITCH

CROSS-REFERENCE

This application is a continuation of International PCT Application No. PCT/EP2017/051866 filed Jan. 27, 2017, which claims priority to Application No. EP16153035.7, filed Jan. 27, 2016, and Application No. EP16178824.5, filed Jul. 11, 2016, the disclosures of which are incorporated herein by reference in their entireties.

FIELD OF THE INVENTION

The present invention relates to the use of positive allosteric modulators of α2 and α3 GABA$_A$ receptors for treatment of itch.

BACKGROUND OF THE INVENTION

Itch (lat. pruritus) is an unpleasant sensation of the skin that elicits the desire to scratch. The intensity of itching can be mild, moderate or severe resulting in sleep disorders, discomfort and increased irritability or general stress. Symptoms of generalized itch may be related to a variety of different reasons. Itching can be provoked or enhanced by a number of chemical substances such as histamine, prostaglandins, proteases, cytokines, neuropeptides, in particular substance P, and bile salts. Some of the substances act directly on the free nerve ending, while others act indirectly through mast cells or other cells. Factors that are believed to enhance the sensation of itching include dryness of the epidermis and dermis, anoxia of tissues, dilation of the capillaries, irritating stimuli, primary skin diseases and psychiatric disorders.

The itching sensation is transmitted from peripheral nerves via the dorsal horn of the spinal cord to the brain. However, inhibitory receptors present in nerve fibres involved in the transmission of the itching signal to the brain are not well studied, although they might represent a promising drug target to alleviate the itching sensation independent of the cause. Most cases of itching are treated with H1-antihistamines, which work reliably if the cause of itching is histamine related. Common causes of histamine-independent itch include, but are not limited to, atopic dermatitis, kidney or liver diseases and treatment with opioids. Other medications used against itching are corticosteroids, gabapentinoides, opioid-receptor antagonists, capsaicin and local anaesthetics, which are either only for topical application or can have unwanted side-effects if used systemically.

The problem underlying the present invention is to provide alternative means for treatment of itching, in particular cases of itching not treatable with antihistamines. This problem is solved by the subject-matter of the independent claims.

SUMMARY OF THE INVENTION

According to a first aspect of the invention a compound for use in the treatment of itch comprising:
general formula

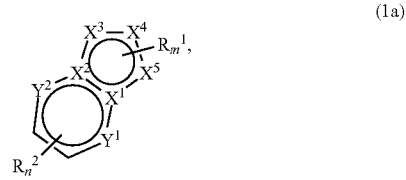
(1a)

general formula or

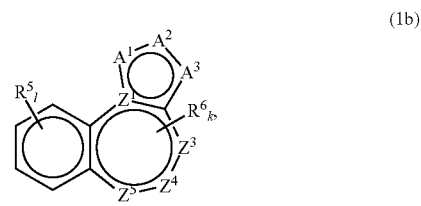
(1b)

general formula

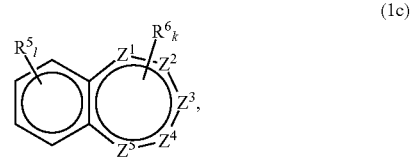
(1c)

in particular formula (1a) and (1b), more particular (1a) is provided, wherein
- $X^1$, $X^2$, $X^3$, $X^4$ and $X^5$ are independently from each other —C, —N, —S or —O wherein at least two of $X^1$, $X^2$, $X^3$, $X^4$ and $X^5$ are —N,
- $Y^1$ and $Y^2$ are independently from each other —C or —N,
- m of $R^1_m$ is 1,
- $R^1$ is a substituted or unsubstituted $C_6$ aryl or —(C=O)—$R^3$, with $R^3$ being a substituted or unsubstituted $C_6$ heteroaryl,
- n of $R^2_n$ is 1 or 2,
- each $R^2$ independently from any other $R^2$ is a substituted or unsubstituted $C_3$-$C_8$ cycloalkyl, a substituted or unsubstituted $C_1$-$C_6$ alkyl, a substituted or unsubstituted $C_1$-$C_6$ alcohol, a substituted or unsubstituted $C_6$ heteroaryl, a halogen, particularly —F, or —O—$CH_2$—$R^4$, with $R^4$ being a substituted or unsubstituted $C_4$ heteroaryl,
- $Z^1$, $Z^2$, $Z^3$, $Z^4$ and $Z^5$ are independently of each other —C, —N, —S or —O,
- $A^1$, $A^2$ and $A^3$, are independently of each other —C, —N or —(C=O)—O—$R^7$, with $R^7$ being an alkyl,
- i of $R^5_i$ is 1 or 2,
- each $R^5$ is independently from each other a $C_1$-$C_4$ alkinyl or a halogen, particularly —Cl,
- k of $R^6_k$ is 1, 2, 3 or 4, in particular 1 or 2,
- each $R^6$ is independently from each other a substituted or unsubstituted aryl, a substituted or unsubstituted heteroaryl, a substituted or unsubstituted $C_1$-$C_3$ alkyl, oxygen or hydrogen.

A $C_1$-$C_6$ alkyl in the context of the present specification signifies a saturated linear or branched hydrocarbon having 1, 2, 3, 4, 5 or 6 carbon atoms, wherein one carbon-carbon bond may be unsaturated and one $CH_2$ moiety may be exchanged for oxygen (ether bridge). Non-limiting examples for a $C_1$-$C_4$ alkyl are methyl, ethyl, propyl, prop-2-enyl, n-butyl, 2-methylpropyl, tert-butyl, but-3-enyl, prop-2-inyl and but-3-inyl.

The term aryl in the context of the present specification signifies a cyclic aromatic $C_5$-$C_{10}$ hydrocarbon. Examples of aryl include, without being restricted to, phenyl, naphthyl and heteroaryl. A heteroaryl in the context of the present invention is an aryl that comprises one or several nitrogen, oxygen and/or sulphur atoms. Examples for heteroaryl include, without being restricted to, pyrrole, thiophene, furan, imidazole, pyrazole, thiazole, oxazole, pyridine, pyrimidine, thiazin, quinoline, benzofuran and indole. An aryl or a heteroaryl in the context of the invention additionally may be substituted by one or more alkyl groups.

As used herein the term "aryl" refers to a hydrocarbon with alternating double and single bonds between the carbon atoms forming a ring structure (in the following an "aromatic hydrocarbon"). The term "heteroaryl" refers to aryl compounds in which at least one carbon atom is replaced with an oxygen, a nitrogen or a sulphur atom. The aromatic hydrocarbon may be neutral or charged. Examples of aryl or hetero aryl groups are benzene, pyridine, pyrrole or cyclopenta-1,3-diene-anion. Aryl or hetero aryl groups as used herein may optionally include further substituent groups.

In the context of the present specification the term allosteric modulator is used in its meaning known in the field of biochemistry and pharmacology; it refers to a substance that indirectly modulates the effects of an agonist at a receptor. A positive allosteric modulator induces an amplification of the agonist's effect, without having an effect by itself in the absence of the agonist. An allosteric modulator binds to a site distinct from the agonist's binding site (allosteric).

In the context of the present specification the term GABA receptor is used in its meaning known in the field of biochemistry; it refers to receptors of the inhibitory neurotransmitter gamma-aminobutyric acid (GABA). Two main types of GABA receptors are known, $GABA_A$ receptors (ionotropic receptors), are ligand-gated ion channels and $GABA_B$ receptors, also known as metabotropic receptors, are G protein-coupled receptors. $GABA_A$ receptors are the most common and most important inhibitory receptors within the central nervous system. $GABA_A$ receptors comprise five subunits that are grouped in eight classes: $\alpha_{1-6}$, $\beta_{1-3}$, $\gamma_{1-3}$, $\delta$, $\varepsilon$, $\pi$, $\theta$ and $\rho_{1-3}$. The majority of $GABA_A$ receptors comprise two $\alpha$, two $\beta$ and one $\gamma$ subunit. The different types of a subunits confer different properties to the $GABA_A$ receptor. Whereas the $\alpha 1$ subunit is among other functions responsible for the sedative effect of benzodiazepines, the $\alpha 2$ subunit is connected to the anxiolytic function of the receptors and the $\alpha 3$ subunit confers the muscle relaxing properties of the $GABA_A$ receptor.

In certain embodiments a compound comprising the general formula (1a) is provided, wherein $X^1$, $X^2$, $X^3$, $X^4$ and $X^5$ are independently from each other —C, —N, —S or —O wherein at least two of $X^1$, $X^2$, $X^3$, $X^4$ and $X^5$ are —N, $Y^1$ and $Y^2$ are independently from each other —C or —N, m of $R^1_m$ is 1, $R^1$ is a substituted or unsubstituted $C_6$ aryl or —(C=O)—$R^3$, with $R^3$ being a substituted or unsubstituted $C_6$ heteroaryl, n of $R^2_n$ is 1 or 2, each $R^2$ independently from any other $R^2$ is a substituted or unsubstituted $C_3$-$C_8$ cycloalkyl, a substituted or unsubstituted $C_1$-$C_6$ alkyl, a substituted or unsubstituted $C_1$-$C_6$ alcohol, a substituted or unsubstituted $C_6$ heteroaryl, a halogen, particularly —F, or —O—$CH_2$—$R^4$, with $R^4$ being a substituted or unsubstituted $C_4$ heteroaryl.

In certain embodiments, a compound comprising the general formula (1b) is provided, wherein $Z^3$, $Z^4$ and $Z^5$ are independently of each other —C, —N, —S or —O, $A^1$, $A^2$ and $A^3$, are independently of each other —C, —N or —(C=O)—O—$R^7$, with $R^7$ being an alkyl, i of $R^5_i$ is 1 or 2, each $R^5$ is independently from each other a $C_1$-$C_4$ alkinyl or a halogen, particularly —Cl, k of $R^6_k$ is 1, 2, 3 or 4, in particular 1 or 2, each $R^6$ is independently from each other a substituted or unsubstituted aryl, a substituted or unsubstituted heteroaryl, a substituted or unsubstituted $C_1$-$C_3$ alkyl, oxygen or hydrogen.

In certain embodiments, a compound comprising the general formula (1c) is provided, wherein $Z^1$, $Z^2$, $Z^3$, $Z^4$ and $Z^5$ are independently of each other —C, —N, —S or —O, i of $R^5_i$ is 1 or 2, each $R^5$ is independently from each other a $C_1$-$C_4$ alkinyl or a halogen, particularly Cl, k of $R^6_k$ is 1, 2, 3 or 4, in particular 1 or 2, each $R^6$ is independently from each other a substituted or unsubstituted aryl, a substituted or unsubstituted heteroaryl, a substituted or unsubstituted $C_1$-$C_3$ alkyl, oxygen or hydrogen.

In certain embodiments, the compound is a positive allosteric $\alpha 2$ and/or $\alpha 3$ $GABA_A$ receptor modulator.

In certain embodiments, the compound for use in the treatment of itch comprises the general formula (1a), general formula (1b) or general formula (1c), wherein $X^1$, $X^2$, $X^3$, $X^4$ and $X^5$ are independently from each other —C, —N, wherein at least two of $X^1$, $X^2$, $X^3$, $X^4$ and $X^5$ are —N, $Y^1$ and $Y^2$ are independently from each other —C or —N, m of $R^1_m$ is 1, $R^1$ is a substituted or unsubstituted $C_6$ aryl or —(C=O)—$R^3$, with $R^3$ being a substituted or unsubstituted $C_6$ heteroaryl, n of $R^2_n$ is 1 or 2, each $R^2$ independently from any other $R^2$ is a substituted or unsubstituted $C_3$-$C_8$ cycloalkyl, a substituted or unsubstituted $C_1$-$C_6$ alkyl, a substituted or unsubstituted $C_1$-$C_6$ alcohol, a substituted or unsubstituted $C_6$ heteroaryl, a halogen, particularly —F, or —O—$CH_2$—$R^4$, with $R^4$ being a substituted or unsubstituted $C_4$ heteroaryl, $Z^1$, $Z^2$, $Z^3$, $Z^4$ and $Z^5$ are independently of each other —C, —N or —O, $A^1$, $A^2$ and $A^3$, are independently of each other —C, —N or —(C=O)—O—$R^7$, with $R^7$ being an alkyl, i of $R^5_i$ is 1 or 2, each $R^5$ is independently from each other a $C_1$-$C_4$ alkinyl or a halogen, particularly Cl, k of $R^6_k$ is 1, 2, 3 or 4, each $R^6$ is independently from each other a substituted or unsubstituted aryl, a substituted or unsubstituted heteroaryl, a substituted or unsubstituted $C_1$-$C_3$ alkyl, oxygen or hydrogen.

In certain embodiments a compound comprising the general formula (1a) is provided, wherein $X^1$, $X^2$, $X^3$, $X^4$ and $X^5$ are independently from each other —C or —N, wherein at least two of $X^1$, $X^2$, $X^3$, $X^4$ and $X^5$ are —N, $Y^1$ and $Y^2$ are independently from each other —C or —N, m of $R^1_m$ is 1, $R^1$ is a substituted or unsubstituted $C_6$ aryl or —(C=O)—$R^3$, with $R^3$ being a substituted or unsubstituted $C_6$ heteroaryl, n of $R^2_n$ is 1 or 2, each $R^2$ independently from any other $R^2$ is a substituted or unsubstituted $C_3$-$C_8$ cycloalkyl, a substituted or unsubstituted $C_1$-$C_6$ alkyl, a substituted or unsubstituted $C_1$-$C_6$ alcohol, a substituted or unsubstituted $C_6$ heteroaryl, a halogen, particularly —F, or —O—$CH_2$—$R^4$, with $R^4$ being a substituted or unsubstituted $C_4$ heteroaryl, In certain embodiments, a compound comprising the general formula (1b) is provided, wherein $Z^3$, $Z^4$ and $Z^5$ are independently of each other —C or —N, $A^1$, $A^2$ and $A^3$, are independently of each other —C, —N or —(C=O)—O—$R^7$, with $R^7$ being an alkyl, i of $R^5_i$ is 1 or 2, each $R^5$ is independently from each other a $C_1$-$C_4$ alkinyl or a halogen, particularly Cl, k of $R^6{}_k$ is 1, 2, 3 or 4, in particular 1 or 2, each $R^6$ is independently from each other a substituted or unsubstituted aryl, a substituted or unsubstituted heteroaryl, a substituted or unsubstituted $C_1$-$C_3$ alkyl, oxygen or hydrogen.

In certain embodiments, a compound comprising the general formula (1c) is provided, wherein $Z^1$, $Z^2$, $Z^3$, $Z^4$ and $Z^5$ are independently of each other —C, —N or —O, i of $R^5$ is 1 or 2, each $R^5$ is independently from each other a $C_1$-$C_4$ alkinyl or a halogen, particularly Cl, k of $R^6{}_k$ is 1, 2, 3 or 4, in particular 1 or 2, each $R^6$ is independently from each other a substituted or unsubstituted aryl, a substituted or unsubstituted heteroaryl, a substituted or unsubstituted $C_1$-$C_3$ alkyl, oxygen or hydrogen.

In certain embodiments, the compound comprises the general formula (2), (3), (4), (5), (6) or (7)

In certain embodiments, the compound comprises the general formula (6) with $Z^1$, $Z^4$, $Z^5$, i of $R^5{}_i$, $R^5$, k of $R^6{}_k$ and $R^6$ having the same meaning as defined above.

In certain embodiments, the compound comprises the general formula (7) with $Z^4$, $Z^5$, i of $R^5{}_i$, $R^5$, k of $R^6{}_k$, $R^6$, $A^1$, $A^2$ and $A^3$ having the same meaning as defined above.

In certain embodiments, the compound comprises the general formula (2a), (3a), (4a), (5a), (5b), (6a), (6b) or (7a)

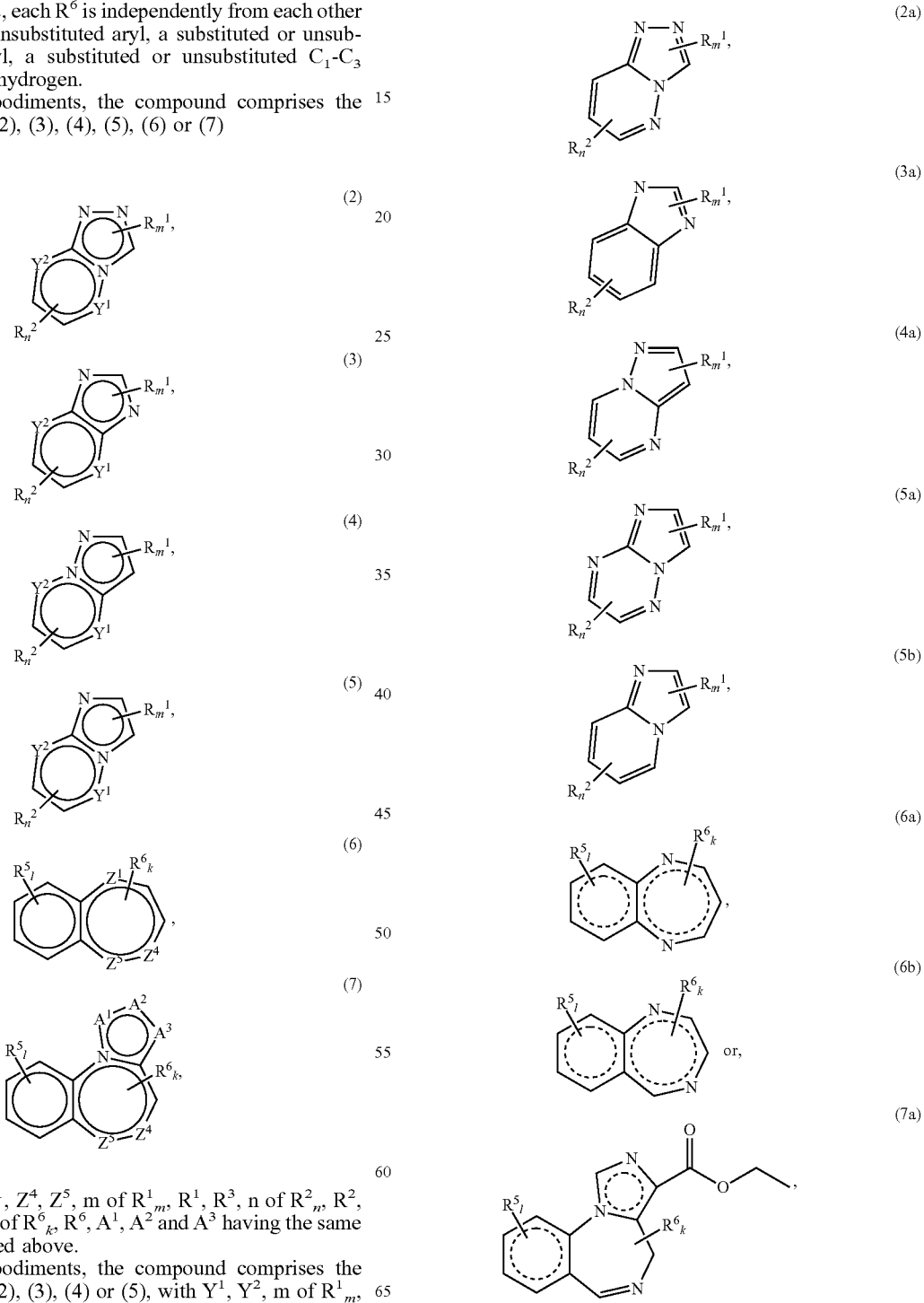

with $Y^1$, $Y^2$, $Z^1$, $Z^4$, $Z^5$, m of $R^1{}_m$, $R^1$, $R^3$, n of $R^2{}_n$, $R^2$, $R^4$, i of $R^5{}_i$, $R^5$, k of $R^6{}_k$, $R^6$, $A^1$, $A^2$ and $A^3$ having the same meaning as defined above.

In certain embodiments, the compound comprises the general formula (2), (3), (4) or (5), with $Y^1$, $Y^2$, m of $R^1{}_m$, $R^1$, $R^3$, n of $R^2{}_n$, $R^2$ and $R^4$ having the same meaning as defined above.

with m of $R^1_m$, $R^1$, $R^3$, n of $R^2_n$, $R^2$, $R^4$, i of $R^5_i$, $R^5$, k of $R^6_k$ and $R^6$ having the same meaning as defined above.

In certain embodiments, the compound comprises the general formula (2a), (3a), (4a), (5a) or (5b) with m of $R^1_m$, $R^1$, $R^3$, n of $R^2_n$, $R^2$ and $R^4$ having the same meaning as defined above.

In certain embodiments, the compound comprises the general formula (6a) or (6b) with m of i of $R^5_i$, $R^5$, k of $R^6_k$ and $R^6$ having the same meaning as defined above.

In certain embodiments, the compound comprises the general formula (7a) with m of i of $R^5_i$, R5, k of $R^6_k$ and $R^6$ having the same meaning as defined above.

In certain embodiments, the compound comprising the general formula 1a, 1b, 1c, 2, 3, 4, 5, 6, 7, 2a, 3a, 4a, 5a, 5b, 6a, 6b or 7a, wherein m of $R^1$ is 1 and $R^1$ is: an unsubstituted phenyl, a substituted phenyl comprising at least one —F as a substituent, an unsubstituted biphenyl, a substituted biphenyl comprising at least one —CN as a substituent, particularly on the phenyl moiety not connected to the parent moiety, or a substituted biphenyl comprising at least one —CN as a substituent, particularly on the phenyl moiety not connected to the parent moiety, wherein in particular one phenyl moiety comprises additionally at least one —F as a substituent, more particularly each phenyl moiety comprises additionally at least one —F as a substituent, or —(C=O)—$R^3$, with $R^3$ being pyridine, and i of $R^5$ is 1 and $R^5$ is Cl, Br, F, or a $C_2$ alkinyl.

In certain embodiments, the compound comprising the general formula 1a, 2, 3, 4, 5, 2a, 3a, 4a, 5a or 5b, wherein m of $R^1$ is 1 and $R^1$ is: an unsubstituted phenyl, a substituted phenyl comprising at least one —F as a substituent, an unsubstituted biphenyl, a substituted biphenyl comprising at least one —CN as a substituent, particularly on the phenyl moiety not connected to the parent moiety, or a substituted biphenyl comprising at least one —CN as a substituent, particularly on the phenyl moiety not connected to the parent moiety, wherein in particular one phenyl moiety comprises additionally at least one —F as a substituent, more particularly each phenyl moiety comprises additionally at least one —F as a substituent, or —(C=O)—$R^3$, with $R^3$ being pyridine.

In certain embodiments, the compound comprising the general formula 1b, 7, or 7a, wherein i of $R^5$ is 1 and $R^5$ is Cl, Br, F, or a $C_2$ alkinyl.

In certain embodiments, the compound comprising the general formula 1c, 6, 6a or 6b, wherein i of $R^5$ is 1 and $R^5$ is Cl, Br, F, or a $C_2$ alkinyl.

In certain embodiments, the compound comprising the general formula 1a, 1b, 1c, 2, 3, 4, 5, 6, 7, 2a, 3a, 4a, 5s, 5b, 6a, 6b or 7a, wherein n of $R^2$ is 1 or 2 and in case of n being 2, each $R^2$ independently from each other is an unsubstituted $C_3$-$C_8$ cycloalkyl, particularly a $C_4$-cycloalkyl, an unsubstituted $C_1$-$C_6$ alkyl, particularly tert-butyl, or —O—$CH_2$—$R^4$, with $R^4$ being a substituted or unsubstituted $C_4$ heteroaryl, in particular $R^4$ being a substituted or unsubstituted triazole, an unsubstituted $C_1$-$C_6$ alcohol, in particular a $C_4$ alcohol, a halogen, in particular —F, in case of n being 1, $R^2$ is an unsubstituted $C_1$-$C_6$ alcohol, in particular a $C_4$ alcohol, an unsubstituted $C_6$ heteroaryl, in particular pyridine, and k of $R^6$ is 1 or 4 and in case of k being 1, $R^6$ is a substituted or unsubstituted aryl, a substituted or unsubstituted heteroaryl, in case of k being 4, each $R^6$ independently from each other is a substituted or unsubstituted aryl, a substituted or unsubstituted $C_1$-$C_3$ alkyl, oxygen, or hydrogen.

In certain embodiments, the compound comprising the general formula 1a, 1b, 1c, 2, 3, 4, 5, 6, 7, 2a, 3a, 4a, 5a, 5b, 6a, 6b or 7a, wherein n of $R^2$ is 1 or 2 and in case of n being 2, each $R^2$ independently from each other is an unsubstituted $C_3$-$C_8$ cycloalkyl, particularly a $C_4$-cycloalkyl, an unsubstituted $C_1$-$C_6$ alkyl, particularly tert-butyl, or —O—$CH_2$—$R^4$, with $R^4$ being a substituted or unsubstituted $C_4$ heteroaryl, in particular $R^4$ being a substituted or unsubstituted triazole, an unsubstituted $C_1$-$C_6$ alcohol, in particular a $C_4$ alcohol, a halogen, in particular —F, in case of n being 1, $R^2$ is an unsubstituted $C_1$-$C_6$ alcohol, in particular a $C_4$ alcohol, an unsubstituted C6 heteroaryl, in particular pyridine, and k of $R^6$ is 1 or 4 and in case of k being 1, $R^6$ is a substituted or unsubstituted aryl, a substituted or unsubstituted heteroaryl, in case of k being 4, each $R^6$ independently from each other is a substituted or unsubstituted aryl, a substituted or unsubstituted $C_1$-$C_3$ alkyl, oxygen, or hydrogen.

In certain embodiments, the compound comprising the general formula 1a, 2, 3, 4, 5, 2a, 3a, 4a, 5a or 5b, wherein n of $R^2$ is 1 or 2 and in case of n being 2, each $R^2$ independently from each other is an unsubstituted $C_3$-$C_8$ cycloalkyl, particularly a $C_4$-cycloalkyl, an unsubstituted $C_1$-$C_6$ alkyl, particularly tert-butyl, or —O—$CH_2$—$R^4$, with $R^4$ being a substituted or unsubstituted $C_4$ heteroaryl, in particular $R^4$ being a substituted or unsubstituted triazole, an unsubstituted $C_1$-$C_6$ alcohol, in particular a $C_4$ alcohol, a halogen, in particular —F, in case of n being 1, $R^2$ is an unsubstituted $C_1$-$C_6$ alcohol, in particular a $C_4$ alcohol, an unsubstituted C6 heteroaryl, in particular pyridine.

In certain embodiments, the compound comprising the general formula 1b, 7, or 7a, wherein k of $R^6$ is 1 or 4 and in case of k being 1, $R^6$ is a substituted or unsubstituted aryl, a substituted or unsubstituted heteroaryl, in case of k being 4, each $R^6$ independently from each other is a substituted or unsubstituted aryl, a substituted or unsubstituted $C_1$-$C_3$ alkyl, oxygen, or hydrogen.

In certain embodiments, the compound comprising the general formula 1c, 6, 6a or 6b wherein k of $R^6$ is 1 or 4 and in case of k being 1, $R^6$ is a substituted or unsubstituted aryl, a substituted or unsubstituted heteroaryl, in case of k being 4, each $R^6$ independently from each other is a substituted or unsubstituted aryl, a substituted or unsubstituted $C_1$-$C_3$ alkyl, oxygen, or hydrogen.

In certain embodiments, the compound comprising the general formula 1a, 1b, 1c, 2, 3, 4, 5, 6, 7, 2a, 3a, 4a, 5s, 5b, 6a, 6b or 7a, wherein n of $R^2$ is 2 and one $R^2$ is an unsubstituted $C_3$-$C_8$ cycloalkyl, particularly a $C_4$-cycloalkyl, or an unsubstituted $C_1$-$C_6$ alkyl, particularly tert-butyl, and the other $R^2$ is —O—$CH_2$—$R^4$, with $R^4$ being a substituted or unsubstituted $C_4$ heteroaryl, in particular a substituted or unsubstituted triazole, or one $R^2$ is an unsubstituted $C_1$-$C_6$ alcohol, in particular a $C_4$ alcohol, and the other $R^2$ is a halogen, in particular —F, and k of $R^6$ is 4 and two $R^6$ are oxygen, the other $R^6$ are independently from each other a substituted or unsubstituted aryl, a substituted or unsubstituted $C_1$-$C_3$ alkyl, or hydrogen.

In certain embodiments, the compound comprising the general formula 1a, 2, 3, 4, 5, 2a, 3a, 4a, 5s or 5b, wherein n of $R^2$ is 2 and one $R^2$ is an unsubstituted $C_3$-$C_8$ cycloalkyl, particularly a $C_4$-cycloalkyl, or an unsubstituted $C_1$-$C_6$ alkyl, particularly tert-butyl, and the other $R^2$ is O—$CH_2$—$R^4$, with $R^4$ being a substituted or unsubstituted $C_4$ heteroaryl, in particular a substituted or unsubstituted triazole, or one $R^2$ is an unsubstituted $C_1$-$C_6$ alcohol, in particular a $C_4$ alcohol, and the other $R^2$ is a halogen, in particular —F.

In certain embodiments, the compound comprising the general formula 1b, 7, or 7a, wherein k of $R^6$ is 4 and two $R^6$ are oxygen, the other $R^6$ are independently from each other a substituted or unsubstituted aryl, a substituted or unsubstituted $C_1$-$C_3$ alkyl, or hydrogen.

In certain embodiments, the compound comprising the general formula 1c, 6, 6a or 6b, wherein k of $R^6$ is 4 and two $R^6$ are oxygen, the other $R^6$ are independently from each other a substituted or unsubstituted aryl, a substituted or unsubstituted $C_1$-$C_3$ alkyl, or hydrogen.

In certain embodiments, the compound comprises the general formula (2a'), (3a'), (4a'), (5a'), (5b'), (6a'), (6b') or (7a')

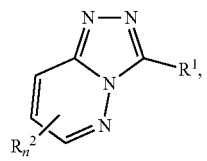
(2a')

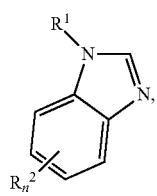
(3a')

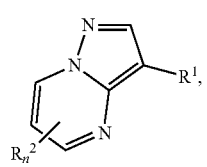
(4a')

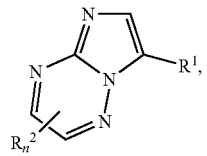
(5a')

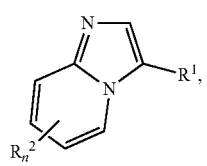
(5b')

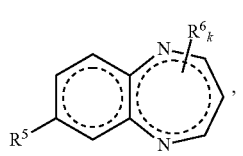
(6a')

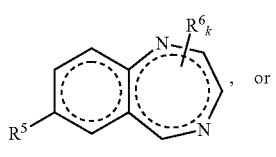
(6b') or

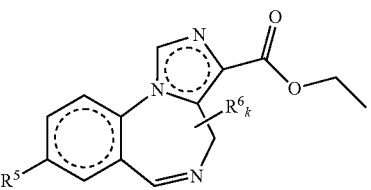
(7a')

with $R^1$, $R^3$ n of $R^2{}_n$, $R^2$, $R^4$, $R^5$, k of $R^6{}_k$ and $R^6$ having the same meaning as defined above.

In certain embodiments, the compound comprises the general formula (2a'), (3a'), (4a'), (5a') or (5b') with $R^1$, $R^3$, n of $R^2{}_n$, $R^2$ and $R^4$ having the same meaning as defined above.

In certain embodiments, the compound comprises the general formula (6a') or (6b') with k of $R^6{}_k$ and $R^6$ having the same meaning as defined above.

In certain embodiments, the compound comprises the general formula (7a') with k of $R^6{}_k$ and $R^6$ having the same meaning as defined above.

In certain embodiments, the compound comprises the general formula (2a'), (3a'), (4a'), (5a'), (5b'), (6a'), (6b') or (7a'), wherein $R^1$ is in case of formula (2a') a substituted or unsubstituted $C_6$ aryl, in particular an unsubstituted phenyl, a substituted phenyl comprising at least one —F as a substituent, in case of formula (3a'), (5a') or (5b'), a substituted or unsubstituted biphenyl, in particular an unsubstituted biphenyl, a substituted biphenyl comprising at least one —CN as a substituent, particularly on the phenyl moiety not connected to the parent moiety, wherein in particular one phenyl moiety comprises additionally at least one —F as a substituent, more particularly each phenyl moiety comprises additionally at least one —F as a substituent, or in case of formula (4a'), —(C=O)—$R^3$, with $R^3$ being a substituted or unsubstituted $C_6$ heteroaryl, in particular with $R^3$ being pyridine, $R^5$ is in case of formula (6a') or (6b'), Cl, Br or F, in case of formula (7a') $C_2$ alkinyl, wherein $R^2{}_n$ and $R^6{}_k$ have the same meaning as defined above.

In certain embodiments, the compound comprises the general formula (2a'), (3a'), (4a'), (5a') or (5b') wherein $R^1$ is in case of formula (2a') a substituted or unsubstituted $C_6$ aryl, in particular an unsubstituted phenyl, a substituted phenyl comprising at least one —F as a substituent, in case of formula (3a'), (5a') or (5b'), a substituted or unsubstituted biphenyl, in particular an unsubstituted biphenyl, a substituted biphenyl comprising at least one —CN as a substituent, particularly on the phenyl moiety not connected to the parent moiety, wherein in particular one phenyl moiety comprises additionally at least one —F as a substituent, more particularly each phenyl moiety comprises additionally at least one —F as a substituent, or in case of formula (4a'), —(C=O)—$R^3$, with $R^3$ being a substituted or unsubstituted $C_6$ heteroaryl, in particular with $R^3$ being pyridine, wherein $R^2{}_n$ has the same meaning as defined above.

In certain embodiments, the compound comprises the general formula (6a') or (6b'), wherein $R^5$ is Cl, Br or F, wherein $R^6{}_k$ has the same meaning as defined above.

In certain embodiments, the compound comprises the general formula (7a'), wherein $R^5$ is $C^2$ alkinyl, wherein $R^6{}_k$ has the same meaning as defined above.

In certain embodiments, the compound comprises the general formula (2a"), (3a"), (4a"), (5a"), (5b") or (7a")

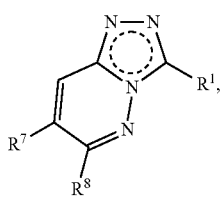
(2a")

-continued

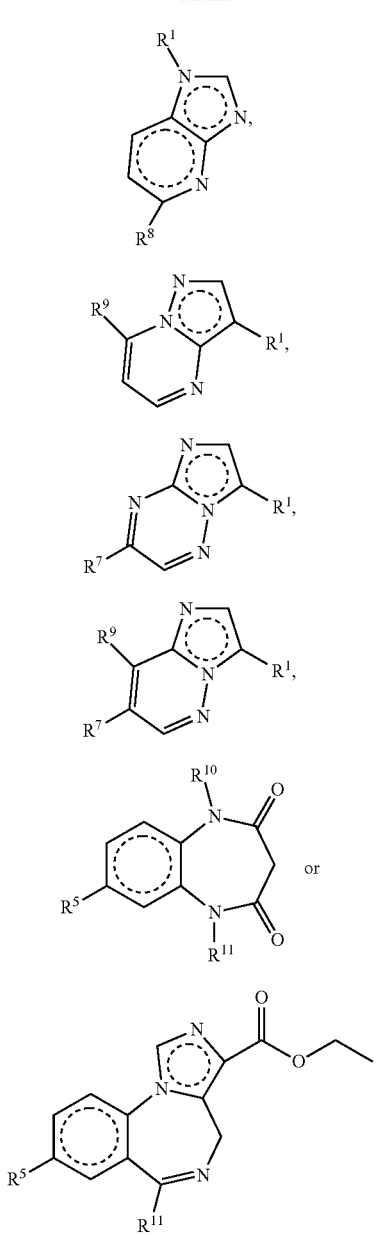

with R$^7$ being an unsubstituted C$_1$-C$_6$ alkyl, particularly tert-butyl, an unsubstituted C$_3$-C$_8$ cycloalkyl, particularly a C$_4$-cycloalkyl, an unsubstituted C$_1$-C$_6$ alcohol, in particular a C$_4$ alcohol, in particular R$^7$ being in case of formula (2a") an unsubstituted C$_1$-C$_6$ alkyl, particularly tert-butyl, or an unsubstituted C$_3$-C$_8$ cycloalkyl, particularly a C$_4$-cycloalkyl, or R$^7$ being in case of formula (5a") or (5b") an unsubstituted C$_1$-C$_6$ alcohol, in particular a C$_4$ alcohol, R$^8$ being —O—CH$_2$—R$^4$, with R$^4$ being a substituted or unsubstituted C$_4$ heteroaryl, in particular a substituted or unsubstituted triazole, or an unsubstituted C$_1$-C$_6$ alcohol, in particular a C$_4$ alcohol, in particular R$^8$ being in case of formula (2a") —O—CH$_2$—R$^4$, with R$^4$ being a substituted or unsubstituted C$_4$ heteroaryl, in particular a substituted or unsubstituted triazole, or R$^8$ being in case of formula (3a") an unsubstituted C$_1$-C$_6$ alcohol, in particular a C$_4$ alcohol, R$^9$ being an unsubstituted C$_6$ heteroaryl, in particular pyridine, or a halogen, in particular —F, R$^9$ being in case of formula (4a") an unsubstituted C$_6$ heteroaryl, in particular pyridine, or R$^9$ being in case of formula (5b") a halogen, in particular —F, R$^{10}$ being a C$_1$-C$_3$ akyl or hydrogen, R$^{11}$ being a substituted or unsubstituted aryl or a substituted or unsubstituted heteroaryl, in particular R$^{11}$ being in case of formula (6a") an substituted or unsubstituted aryl, in particular phenyl R$^{11}$ being in case of formula (7a") a substituted or unsubstituted heteroaryl, in particular pyridine, a substituted or unsubstituted aryl, in particular phenyl, R$^5$ being in case of formula (6a"), Cl, Br or F, in case of formula (7a") C$_2$ alkinyl.

In certain embodiments, the compound comprises the general formula (2a"), (3a"), (4a"), (5a") or (5b") with R$^7$ being an unsubstituted C$_1$-C$_6$ alkyl, particularly tert-butyl, an unsubstituted C$_3$-C$_8$ cycloalkyl, particularly a C$_4$-cycloalkyl, an unsubstituted C$_1$-C$_6$ alcohol, in particular a C$_4$ alcohol, in particular R$^7$ being in case of formula (2a") an unsubstituted C$_1$-C$_6$-alkyl, particularly tert-butyl, or an unsubstituted C$_3$-C$_8$ cycloalkyl, particularly a C$_4$-cycloalkyl, or R$^7$ being in case of formula (5a") or (5b") an unsubstituted C$_1$-C$_6$ alcohol, in particular a C$_4$ alcohol, R$^8$ being —O—CH$_2$—R$^4$, with R$^4$ being a substituted or unsubstituted C$_4$ heteroaryl, in particular a substituted or unsubstituted triazole, or an unsubstituted C$_1$-C$_6$ alcohol, in particular a C$_4$ alcohol, in particular R$^8$ being in case of formula (2a") —O—CH$_2$—R$^4$, with R$^4$ being a substituted or unsubstituted C$_4$ heteroaryl, in particular a substituted or unsubstituted triazole, or R$^8$ being in case of formula (3a") an unsubstituted C$_1$-C$_6$ alcohol, in particular a C$_4$ alcohol, R$^9$ being an unsubstituted C$_6$ heteroaryl, in particular pyridine, or a halogen, in particular —F, R$^9$ being in case of formula (4a") an unsubstituted C$_6$ heteroaryl, in particular pyridine, or R$^9$ being in case of formula (5b") a halogen, in particular —F.

In certain embodiments, the compound comprises the general formula (6a") with R$^{10}$ being a C$_1$-C$_3$ akyl or hydrogen, R$^{11}$ being a substituted or unsubstituted aryl or a substituted or unsubstituted heteroaryl, in particular R$^{11}$ being in case of formula (6a") an substituted or unsubstituted aryl, in particular phenyl R$^{11}$ being in case of formula (7a") a substituted or unsubstituted heteroaryl, in particular pyridine, R$^5$ being Cl, Br or F.

In certain embodiments, the compound comprises the general formula (7a") with R$^{11}$ being a substituted or unsubstituted aryl or a substituted or unsubstituted heteroaryl, in particular being in case of formula (6a") an substituted or unsubstituted aryl, in particular phenyl R$^{11}$ being in case of formula (7a") a substituted or unsubstituted heteroaryl, in particular pyridine, R$^5$ being C$_2$ alkinyl.

In certain embodiments, the compound comprises the general formula (2a"), (3a"), (4a"), (5a") or (5b") with in case of formula (2a") R$^1$ being or an unsubstituted phenyl, a substituted phenyl comprising at least one —F as a substituent, R$^7$ being an unsubstituted C$_1$-C$_6$ alkyl, particularly tert-butyl, or an unsubstituted C$_3$-C$_8$ cycloalkyl, particularly a C$_4$-cycloalkyl, and R$^8$ being —O—CH$_2$—R$^4$, with R$^4$ being a substituted or unsubstituted C$_4$ heteroaryl, in particular a substituted or unsubstituted triazole, in case of formula (3a") R$^1$ being an unsubstituted biphenyl, a substituted biphenyl comprising at least one —CN as a substituent, particularly on the phenyl moiety not connected to the parent moiety, wherein in particular one phenyl moiety comprises additionally at least one —F as a substituent, more particularly each phenyl moiety comprises additionally at least one —F as a substituent, R$^8$ being an unsubstituted $C_1$-$C_6$ alcohol, in particular a $C_4$ alcohol, in case of formula (4a") $R^1$ being —(C=O)—$R^3$, with $R^3$ being an unsubstituted $C_6$ heteroaryl, in particular $R^3$ being pyridine, and $R^9$ being an unsubstituted $C_6$ heteroaryl, in particular pyridine, in case of formula (5a") $R^1$ being an unsubstituted biphenyl, a substituted biphenyl comprising at least one —CN as a substituent, particularly on the phenyl moiety not connected to the parent moiety, wherein in particular one phenyl moiety comprises additionally at least one —F as a substituent, more particularly each phenyl moiety comprises additionally at least one —F as a substituent, $R^7$ being an unsubstituted $C_1$-$C_6$ alcohol, in particular a $C_4$ alcohol, in case of formula (5a") $R^1$ being an unsubstituted biphenyl, a substituted biphenyl comprising at least one —CN as a substituent, particularly on the phenyl moiety not connected to the parent moiety, wherein in particular one phenyl moiety comprises additionally at least one —F as a substituent, more particularly each phenyl moiety comprises additionally at least one —F as a substituent, $R^7$ being an unsubstituted $C_1$-$C_6$ alcohol, in particular a $C_4$ alcohol, $R^9$ being a halogen, in particular —F.

Figure 11:
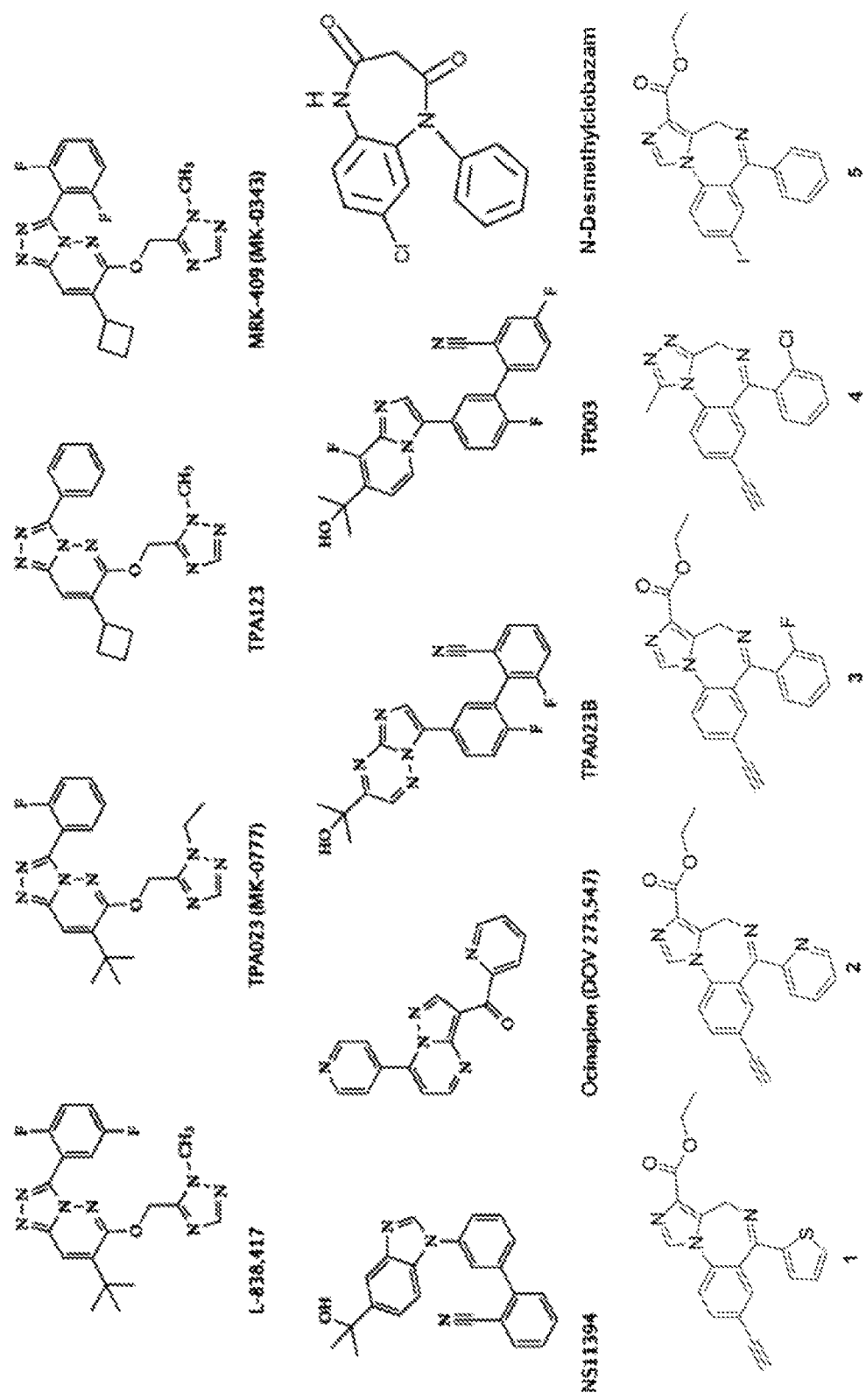

In certain embodiments, the compound is selected from the compounds depicted in FIG. 11, namely L-838417, TPA023 (MK-0777), TPA123, MRK-409(MK-0343), NS11394, Ocinaplon(DOV-273547), TPA023B, TP003, N-Desmethylclobazam, 1, 2, 3, 4 and 5.

In certain embodiments, compound according to the first aspect of the invention for use in preventing Serotonin-, Histamine-, Chloroquine-, Compound48/80- and bile acid-induced itch, in particular Serotonin-, Chloroquine-, Compound48/80- and bile acid-induced itch, more particularly Serotonin-induced itch.

According to a second aspect of the invention an α2 or α3 GABA-modulator for use in the treatment of itch, in particular a modulator according to the first aspect of the invention is provided.

In the following, subaspects of the invention are described. Formula (1c) and (VI) of the subapacts correspond to formula (1c) and (6), respectively. The substituents of the compounds according to formula (1c) or (VI) have been renumbered—due to clarity reasons—compared to formula (1c) and (6). $R^5$ and $R^6$ of formula (1c) are now referred to as $R^{12}_p$ and $R^{13}_q$ in formula (1c). $R^{11}$ of formula (6) is now referred to as $R^{14}$ in formula (VI).

According to a first subaspect of the invention, a compound for use in the treatment of itch is provided, wherein the compound comprises the general formula (1a), general formula (1b) or general formula (1c),

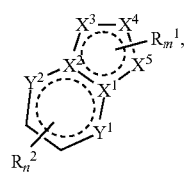
(1a)

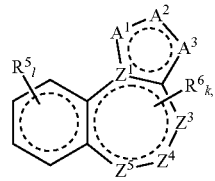
(1b)

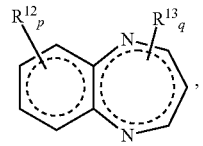
(1c)

in particular formula (1a) and (1b), more particular (1a), wherein $X^1$, $X^2$, $X^3$, $X^4$ and $X^5$ are independently from each other —C, —N, —S or —O wherein at least two of $X^1$, $X^2$, $X^3$, X and $X^5$ are —N, $Y^1$ and $Y^2$ are independently from each other —C or —N, m of $R^1_m$ is 1, $R^1$ is an unsubstituted phenyl, a phenyl substituted with $C_1$-$C_4$-alkyl, F, Cl, Br, I, —CN, a substituted or unsubstituted biphenyl or —(C=O)—$R^3$, with $R^3$ being a substituted or unsubstituted aryl or 5- to 6-membered heteroaryl, in particular a $C_6$ aryl or 6-membered heteroaryl, more particularly a 6-membered heteroaryl, n of $R^2$, is 1 or 2, each $R^2$ independently from any other $R^2$ is a substituted or unsubstituted $C_3$-$C_8$ cycloalkyl, a substituted or unsubstituted $C_1$-$C_6$ alkyl, a substituted or unsubstituted $C_1$-$C_6$ alcohol, a substituted or unsubstituted 6-membered heteroaryl, a halogen, particularly —F, or —O—$CH_2$—$R^4$, with $R^4$ being a substituted or unsubstituted 5- or 6-membered heteroaryl, in particular a 5-membered heteroaryl, $Z^1$, $Z^3$, $Z^4$ and $Z^5$ are independently of each other —C, —N, —S or —O, in particular $Z^1$ is —C or —N and $Z^3$ and $Z^4$ are —C, —N, —S or —O, $A^1$ and $A^2$, are independently of each other —C, —N or —(C=O)—O—$R^{7'}$ and $A^3$ is —(C=O)—O—$R^{7'}$, with $R^{7'}$ being an $C_1$-$C_6$-alkyl, in particular $A^1$ and $A^2$ are independently of each other —C or —N and $A^3$ is —(C=O)—O—$R^{7'}$, with $R^{7'}$ being an $C_1$-$C_6$-alkyl, in particular a $C_1$-$C_2$-alkyl, more particularly a $C_2$-alkyl, i of $R^5_i$ is 1 or 2 each $R^5$ is independently from each other a $C_1$-$C_4$ alkinyl or a halogen, k of $R^6_k$ is 1, 2, 3 or 4, in particular 1 or 2, each $R^6$ is independently from each other a substituted or unsubstituted aryl, a substituted or unsubstituted heteroaryl, a substituted or unsubstituted $C_1$-$C_3$ alkyl, oxygen or hydrogen, in particular a substituted or unsubstituted aryl, a substituted or unsubstituted heteroaryl, a substituted or unsubstituted $C_1$-$C_3$ alkyl, more particularly a substituted or unsubstituted aryl, a substituted or unsubstituted heteroaryl, p of $R^{12}$ is 1 or 2, in particular 1, $R^{12}$ is independently from each other a substituted or unsubstituted $C_1$-$C_4$-alkyl, I, Br, Cl or F, q of $R^{13}$ is 1, 2, 3 or 4, $R^{13}$ is independently from each other a substituted or unsubstituted aryl, a substituted or unsubstituted heteroaryl, a substituted or unsubstituted $C_1$-$C_3$ alkyl, oxygen or hydrogen.

In certain embodiments, the compound for use in the treatment of itch is a positive allosteric α2 and/or α3 $GABA_A$ receptor modulator.

In certain embodiments, the compound for use in the treatment of itch comprises the general formula (1a), general formula (1b) or general formula (1c), in particular formula (1a) and (1b), more particular (1a), wherein $X^1$, $X^2$, $X^3$, $X^4$ and $X^5$ are independently from each other —C or —N, wherein at least two of $X^1$, $X^2$, $X^3$, $X^4$ and $X^5$ are —N, $Y^1$ and $Y^2$ are independently from each other —C or —N, m of $R^1_m$ is 1, $R^1$ is an unsubstituted phenyl, a phenyl substituted with $C_1$-$C_4$-alkyl, F, Cl, Br, I, —CN, a substituted or unsubstituted biphenyl or —(C=O)—$R^3$, with $R^3$ being a substituted or unsubstituted aryl or 5- to 6-membered heteroaryl, in particular a $C_6$ aryl or 6-membered heteroaryl, more particularly a 6-membered heteroaryl, n of $R^2_n$ is 1 or 2, each R2 independently from any other $R^2$ is a substituted or unsubstituted $C_3$-$C_8$ cycloalkyl, a substituted or unsubstituted $C_1$-$C_6$ alkyl, a substituted or unsubstituted $C_1$-$C_6$ alcohol, a substituted or unsubstituted 6-membered heteroaryl, a halogen, particularly —F, or —O—$CH_2$—$R^4$, with $R^4$ being a substituted or unsubstituted 5- or 6-membered heteroaryl, in particular a 5-membered heteroaryl, $Z^1$, $Z^3$, $Z^4$ and $Z^5$ are independently of each other —C, or —N, $A^1$ and $A^2$ are independently of each other —C or —N and $A^3$ is —(C=O)—O—$R^{7'}$, with $R^{7'}$ being a $C_1$-$C_4$-alkyl, in particular a $C_1$-$C_2$-alkyl, more particularly a $C_2$-alkyl, i of $R^5_i$ is 1 or 2 each $R^5$ is independently from each other a $C_1$-$C_4$ alkinyl or a halogen, k of $R^6_k$ is 1, 2, 3 or 4, in particular 1 or 2 each $R^6$ is independently from each other a substituted or unsubstituted aryl, a substituted or unsubstituted heteroaryl, a substituted or unsubstituted $C_1$-$C_3$ alkyl, oxygen or hydrogen, in particular a substituted or unsubstituted aryl, a substituted or unsubstituted heteroaryl, a substituted or unsubstituted $C_1$-$C_3$ alkyl, more particularly a substituted or unsubstituted aryl, a substituted or unsubstituted heteroaryl, p of $R^{12}$ is 1, $R^{12}$ is a substituted or unsubstituted $C_1$-$C_4$-alkyl, I, Br, Cl or F, q of $R^{13}$ is 1, 2, 3 or 4, $R^{13}$ is independently from each other a substituted or unsubstituted aryl, a substituted or unsubstituted heteroaryl, a substituted or unsubstituted $C_1$-$C_3$ alkyl, oxygen or hydrogen.

In certain embodiments, the compound according to the first subaspect comprises the general formula (2), (3), (4), (5), (1c) or (7), in particular (2), (3), (4), (5) or (7), more particularly (2), (3), (4) or (5),

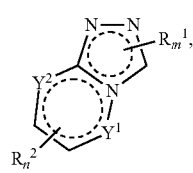
(2)

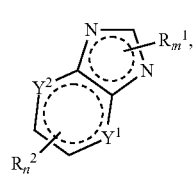
(3)

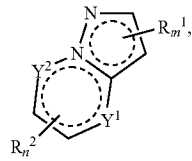
(4)

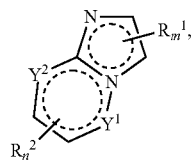
(5)

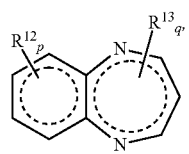
(1c)

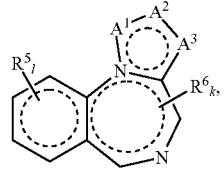
(7)

with $Y^1$, $Y^2$, $Z^4$, $Z^5$, m or $R^1_m$, $R^1$, $R^3$, n of $R^2_n$, $R^2$, $R^4$, p of $R^{12}$, q of $R^{13}$, $R^{13}$, i of $R^5_i$, $R^5$, k of $R^6_k$, $R^6$, $A^1$, $A^2$ and $A^3$ having the same meaning as defined above.

In certain embodiments, the compound according to the first subaspect comprises the general formula (2a), (3a), (4a), (5a), (5b), (1c) or (7a), in particular (2a) (3a) (4a) (5a) (5b) or (7a), more particularly (2a), (3a) (4a), (5a) or (5b).

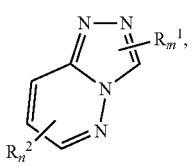
(2a)

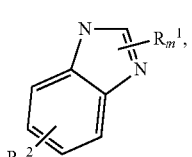
(3a)

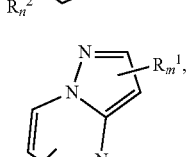
(4a)

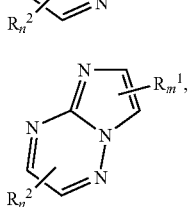
(5a)

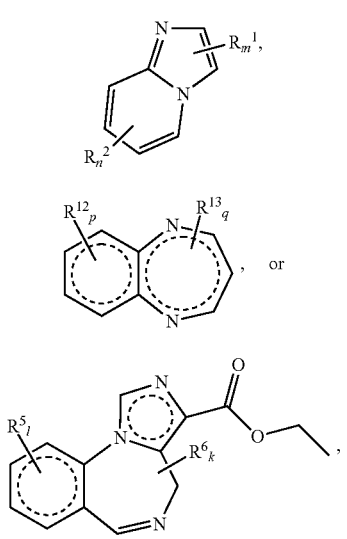

with m of $R^1_m$, $R^1$, $R^3$, n of $R^2_n$, $R^2$, $R^4$, p of $R^{12}_p$, $R^{12}$, q of $R^{13}_q$, $R^{13}$, i of $R^5_i$, $R^5$, k of $R^6_k$ and $R^6$ having the same meaning as defined above.

In certain embodiments, m of $R^1$ is 1 and $R^1$ is: an unsubstituted phenyl, a substituted phenyl comprising $C_1$-$C_4$-alkyl, F, Cl, Br, I, —CN as substituents, wherein in particular said substituted phenyl comprises at least one —F as a substituent, an unsubstituted biphenyl, a substituted biphenyl comprising at least one —CN as a substituent, particularly on the phenyl moiety not connected to the parent moiety, or a substituted biphenyl comprising at least one —CN as a substituent, particularly on the phenyl moiety not connected to the parent moiety, wherein in particular one phenyl moiety comprises additionally at least one —F as a substituent, more particularly each phenyl moiety comprises additionally at least one —F as a substituent, or —(C=O)—$R^3$, with $R^3$ being pyridine.

In certain embodiments, m of $R^1$ is 1 and $R^1$ is a substituted phenyl comprising $C_1$-$C_4$-alkyl, F, Cl, Br, I, —CN as substituents, wherein in particular said substituted phenyl comprises at least one —F as a substituent. The substituted phenyl is a phenyl moiety according to formula (8),

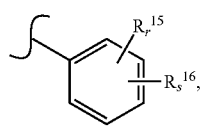

(8)

wherein r is 1, 2, 3, 4 or 5 and $R^{15}$ is F and s is 0, 1, 2, 3 or 4 and $R^{16}$ is $C_1$-$C_4$-alkyl, Cl, Br, I, —CN, wherein the sum of r and s does not exceed 5.

In certain embodiments, m of $R^1$ is 1 and $R^1$ is a substituted phenyl according to formula (8), wherein r is 1 or 2 and $R^{15}$ is F and wherein s is 0, 1, 2, 3 or 4 (in case of r being 2 s is 0, 1, 2 or 3) and $R^{16}$ is $C_1$-$C_4$-alkyl, Cl, Br, I, —CN.

In certain embodiments, m of $R^1$ is 1 and $R^1$ is a substituted phenyl according to formula (8), wherein r is 1 or 2 and $R^{15}$ is F and wherein s is 0.

In certain embodiments, m of $R^1$ is 1 and $R^1$ is a substituted biphenyl comprising at least one —CN as a substituent, particularly on the phenyl moiety not connected to the parent moiety. The substituted biphenyl is a biphenyl moiety according to formula (9),

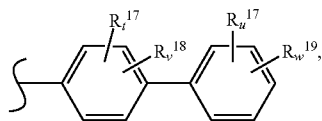

(9)

wherein t is 0, 1, 2, 3 or 4, u is 0, 1, 2, 3, 4 or 5 and $R^{17}$ is —CN, wherein at least t and/or u is equal or greater 1, v is 0, 1, 2, 3 or 4 and $R^{18}$ is $C_1$-$C_4$-alkyl, Cl, Br, I or —CN, and w is 0, 1, 2, 3, 4 or 5 and $R^{19}$ is $C_1$-$C_4$-alkyl, Cl, Br, I or —CN, wherein the sum of t, u, v and w does not exceed 9.

In certain embodiments, m of $R^1$ is 1 and $R^1$ is a substituted biphenyl according to formula (9), wherein v and w are 0 or 1, $R^{18}$ and $R^{19}$ are $C_1$-$C_4$-alkyl, Cl, Br, I or —CN, t and/or u are 1 and $R^{17}$ is —CN.

In certain embodiments, m of $R^1$ is 1 and $R^1$ is a substituted biphenyl according to formula (9), wherein v and w are 0, t and/or u are 1 and $R^{17}$ is —CN.

In certain embodiments, m of R is 1 and R1 is a substituted biphenyl according to formula (9), wherein v, w and t are 0, u is 1 and $R^{17}$ is —CN.

In certain embodiment, m of $R^1$ is 1 and $R^1$ is a substituted biphenyl comprising at least one —CN as a substituent, particularly on the phenyl moiety not connected to the parent moiety, wherein in particular one phenyl moiety comprises additionally at least one —F as a substituent, more particularly each phenyl moiety comprises additionally at least one substituent. This substituted biphenyl is a biphenyl moiety according to formula (10),

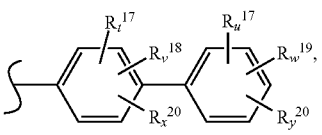

(10)

wherein t is 0, 1, 2, 3 or 4, u is 0, 1, 2, 3, 4 or 5 and $R^{17}$ is —CN, wherein at least t and/or u is equal or greater 1, v is 0, 1, 2, 3 or 4 and $R^{18}$ is $C_1$-$C_4$-alkyl, Cl, Br, I or —CN, w is 0, 1, 2, 3, 4 or 5 and $R^{19}$ is $C_1$-$C_4$-alkyl, Cl, Br, I or —CN, x is 0, 1, 2, 3, or 4, y is 0, 1, 2, 3, 4 or 5 and $R^{20}$ is F, wherein at least x and/or y is equal or greater 1 wherein the sum of t, u, v, w, x and y does not exceed 9.

In certain embodiments, m of $R^1$ is 1 and $R^1$ is a substituted biphenyl according to formula (10), wherein v and w are 0, t and/or u are 1, $R^{17}$ is —CN, x and/or y are 1 and $R^{20}$ is —F.

In certain embodiments, m of $R^1$ is 1 and $R^1$ is a substituted biphenyl according to formula (10), wherein v, w and t are 0, u is 1, $R^{17}$ is —CN, x and/or y are 1 and $R^{20}$ is —F.

In certain embodiments, m of $R^1$ is 1 and $R^1$ is a substituted biphenyl according to formula (10), wherein v, w and t are 0, u is 1, $R^7$ is —CN, x and y are 1 and $R^{20}$ is —F.

In certain embodiments, n of $R^2$ is 1 or 2 and $R^2$ is an unsubstituted $C_3$-$C_8$ cycloalkyl, particularly a $C_4$-cycloalkyl, an unsubstituted $C_1$-$C_6$ alkyl, particularly tert-butyl, or —O—$CH_2$—$R^4$, with $R^4$ being a substituted or unsubstituted 5-membered heteroaryl, in particular $R^4$ being a substituted or unsubstituted triazole, an unsubstituted $C_1$-$C_6$ alcohol, in particular a $C_3$ alcohol, more particularly isopropanol, a halogen, in particular —F, an unsubstituted 6-membered heteroaryl, in particular pyridine.

In certain embodiments, n of $R^2$ is 2 and one $R^2$ is an unsubstituted $C_3$-$C_8$ cycloalkyl, particularly a $C_4$-cycloalkyl, or an unsubstituted $C_1$-$C_6$ alkyl, particularly tert-butyl, and the other $R^2$ is O—$CH_2$—$R^4$, with $R^4$ being a substituted or unsubstituted 5-membered heteroaryl, in particular a substituted or unsubstituted triazole, In certain embodiments, n of $R^2$ is 2 and one $R^2$ is an unsubstituted $C_1$-$C_6$ alcohol, in particular a $C_3$ alcohol, more particularly isopropanol, and the other $R^2$ is a halogen, in particular —F.

In certain embodiments, n of $R^2$ is 1 and $R^2$ is an unsubstituted $C_1$-$C_6$ alcohol or an unsubstituted 6-membered heteroaryl.

In certain embodiments, n of $R^2$ is 1 and $R^2$ is a $C_3$ alcohol or pyridine.

In certain embodiments, n of $R^2$ is 1 and $R^2$ is a $C_3$ alcohol.

In certain embodiments, n of $R^2$ is 1 and $R^2$ is isopropanol.

In certain embodiments, i of $R^5$ is 1 and $R^5$ is I, Cl, Br, F, or a $C_2$ alkinyl.

In certain embodiments, i of $R^5$ is 1 and $R^5$ is —I or a $C_2$ alkinyl.

In certain embodiments, k of $R^6$ is 1 and $R^6$ is a substituted or unsubstituted aryl, a substituted or unsubstituted heteroaryl, a substituted or unsubstituted $C_1$-$C_3$ alkyl.

In certain embodiments, k of $R^6$ is 1 and $R^6$ is a substituted or unsubstituted $C_6$ aryl, a 5- to 6-membered substituted or unsubstituted heteroaryl.

In certain embodiments, k of $R^6$ is 1 and $R^6$ is a phenyl, a phenyl substituted with F or $C_1$, thiophen or pyridine.

In certain embodiments, the compound according to the first subaspect comprises the general formula (2a'), (3a'), (4a'), (5a'), (5b'), (VI) or (7a'), in particular (2a'), (3a'), (4a'), (5a'), (5b') or (7a'), even more particularly (2a'), (3a'), (4a'), (5a') or (5b'),

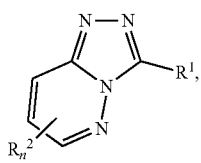
(2a')

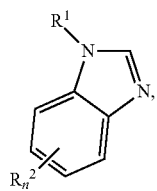
(3a')

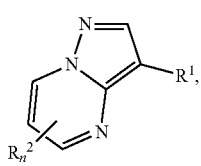
(4a')

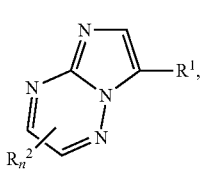
(5a')

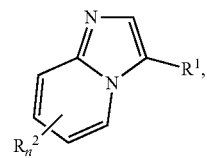
(5b')

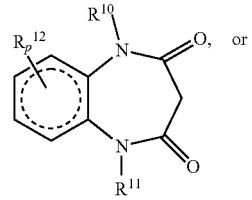
(VI)

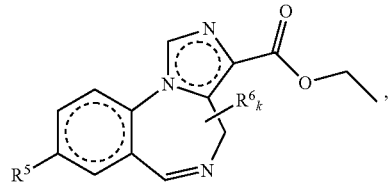
(7a')

wherein $R^{10}$ is a substituted or unsubstituted aryl, a substituted or unsubstituted $C_1$-$C_3$ alkyl or hydrogen, in particular hydrogen, $R^{11}$ is a substituted or unsubstituted aryl, a substituted or unsubstituted $C_1$-$C_3$ alkyl, or hydrogen, in particular a substituted or unsubstituted aryl, more particularly phenyl, p of $R^{12}$ is 1 and $R^{12}$ is I, Br, Cl or F, in particular Cl, with $R^1$, $R^3$, n of $R^2_n$, $R^2$, $R^4$, $R^{10}$, $R^{11}$, p of $R^{12}$, $R^{12}$, $R^5$, k of $R^6_k$ and $R^6$ having the same meaning as defined above.

In certain embodiments, the compound according to the first subaspect comprises the general formula (2a'), (3a'), (4a'), (5a'), (5b'), (VI) or (7a'), in particular (2a'), (3a'), (4a'), (5a'), (5b') or (7a'), even more particularly (2a'), (3a'), (4a'), (5a') or (5b'), wherein $R^1$ is in case of formula (2a')

a substituted or unsubstituted $C_6$ aryl, in particular an unsubstituted phenyl, a substituted phenyl comprising $C_1$-$C_4$-alkyl, F, Cl, Br, I, —CN as substituents, wherein in particular said substituted phenyl comprises at least one —F as a substituent, in case of formula (3a'), (5a') or (5b'), a substituted or unsubstituted biphenyl, in particular an unsubstituted biphenyl, a substituted biphenyl comprising at least one —CN as a substituent, particularly on the phenyl moiety not connected to the parent moiety, wherein in particular one phenyl moiety comprises additionally at least one —F as a substituent, more particularly each phenyl moiety comprises additionally at least one —F as a substituent, or in case of formula (4a'), —(C=O)—$R^3$, with $R^3$ being a substituted or unsubstituted $C_6$ heteroaryl, in particular with $R^3$ being pyridine, $R^5$ is
in case of formula (7a')
$C_2$ alkinyl or I, in particular a $C_2$ alkinyl,
wherein $R^2n$, $R^{10}$, $R^{11}$ and $R^{12}$, and $R^6{}_k$ have the same meaning as defined above.

In certain embodiments, the compound comprises the general formula (2a"), (3a"), (4a"), (5a"), (5b"), (VIa") or (7a"), in particular (2a"), (3a"), (4a"), (5a"), (5b") or (7a"), more particularly (2a"), (3a"), (4a"), (5a") or (5b"),

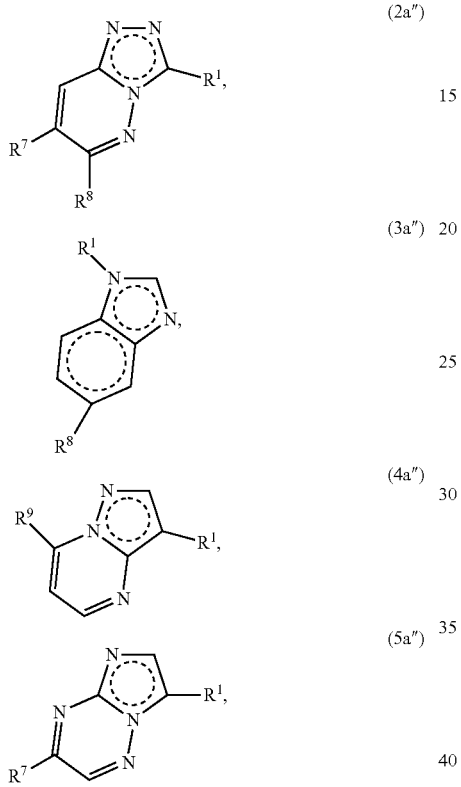

with $R^1$ having the same meaning as defined above, and
$R^7$ being
an unsubstituted $C_1$-$C_6$ alkyl, particularly tert-butyl,
an unsubstituted $C_3$-$C_8$ cycloalkyl, particularly a $C_4$-cycloalkyl,
an unsubstituted $C_1$-$C_6$ alcohol, in particular a $C_3$ alcohol, in particular
$R^7$ being in case of formula (2a")
an unsubstituted $C_1$-$C_6$ alkyl, particularly tert-butyl, or
an unsubstituted $C_3$-$C_8$ cycloalkyl, particularly a $C_4$-cycloalkyl, or
$R^7$ being in case of formula (5a") or (5b")
an unsubstituted $C_1$-$C_6$ alcohol, in particular a $C_3$ alcohol,
$R^1$ being
—O—$CH_2$—$R^4$, with $R^4$ being a substituted or unsubstituted 5-membered heteroaryl, in particular a substituted or unsubstituted triazole, or an unsubstituted $C_1$-$C_6$ alcohol, in particular a $C_3$ alcohol, in particular
$R^8$ being in case of formula (2a")
—O—$CH_2$—$R^4$, with $R^4$ being a substituted or unsubstituted 5-membered heteroaryl, in particular a substituted or unsubstituted triazole, or $R^8$ being in case of formula (3a")
an unsubstituted $C_1$-$C_6$ alcohol, in particular a $C_3$ alcohol,
$R^9$ being
an unsubstituted $C_6$ heteroaryl, in particular pyridine, or a halogen, in particular —F,
a halogen, in particular —F,
$R^9$ being in case of formula (4a")
an unsubstituted 6-membered heteroaryl, in particular pyridine, or
$R^9$ being in case of formula (5b")
a halogen, in particular —F,
$R^{10}$ being
a $C_1$-$C_3$ alkyl or hydrogen, in particular hydrogen
$R^{11}$ being a substituted or unsubstituted aryl or heteroaryl, in particular pyridine, thiophene, a phenyl or a phenyl substituted with F or Cl,
$R^{14}$ being a substituted or unsubstituted aryl or heteroaryl, in particular a substituted or unsubstituted aryl, more particularly phenyl
$R^{12}$ being I, Cl, Br or F, in particular Cl,
$R^5$ being $C_2$ alkinyl or I, in particular $C_2$ alkinyl.

In certain embodiments, the compound comprises the general formula (2a"), (3a"), (4a"), (5a") or (5b")

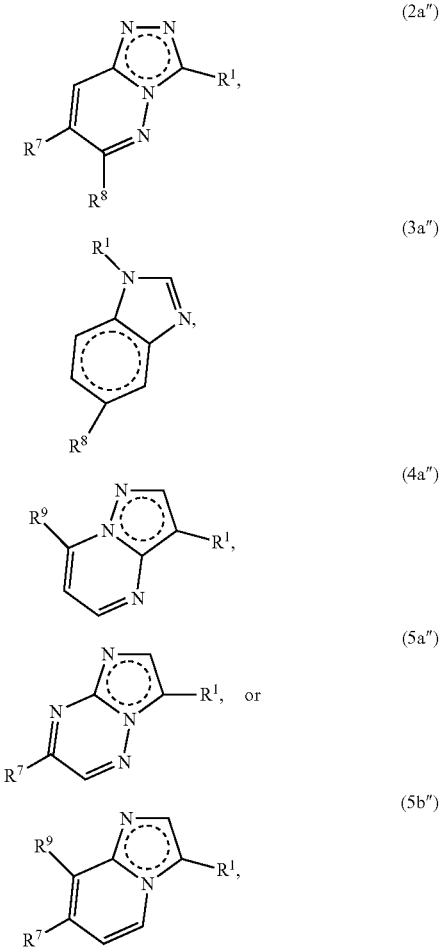

with
in case of formula (2a")
R$^1$ being
an unsubstituted phenyl,
a substituted phenyl comprising C$_1$-C$_4$-alkyl, F, Cl, Br, I, —CN as substituents, wherein in particular said substituted phenyl comprises at least one —F as a substituent,
R$^7$ being
an unsubstituted C$_1$-C$_6$ alkyl, particularly tert-butyl, or
an unsubstituted C$_3$-C$_8$ cycloalkyl, particularly a C$_4$-cycloalkyl, and
R$^8$ being
—O—CH$_2$—R$^4$, with R$^4$ being a substituted or unsubstituted 5-membered heteroaryl, in particular a substituted or unsubstituted triazole,
in case of formula (3a")
R$^1$ being
an unsubstituted biphenyl,
a substituted biphenyl comprising at least one —CN as a substituent, particularly on the phenyl moiety not connected to the parent moiety, or
a substituted biphenyl comprising at least one —CN as a substituent, particularly on the phenyl moiety not connected to the parent moiety, wherein in particular one phenyl moiety comprises additionally at least one —F as a substituent, more particularly each phenyl moiety comprises additionally at least one —F as a substituent,
wherein in particular R$^1$ being
a substituted biphenyl comprising at least one —CN as a substituent, particularly on the phenyl moiety not connected to the parent moiety,
FT being
an unsubstituted C$_1$-C$_6$ alcohol, in particular a C$_3$ alcohol, more particularly isopropanol,
in case of formula (4a")
R$^1$ being
—(C=O)—R$^3$, with R$^3$ being an unsubstituted 6-membered heteroaryl, in particular R$^3$ being pyridine, and
R$^9$ being
being an unsubstituted C$_6$ heteroaryl, in particular pyridine,
in case of formula (5a")
R$^1$ being
an unsubstituted biphenyl,
a substituted biphenyl comprising at least one —CN as a substituent, particularly on the phenyl moiety not connected to the parent moiety, wherein in particular one phenyl moiety comprises additionally at least one —F as a substituent, more particularly each phenyl moiety comprises additionally at least one —F as a substituent,
wherein in particular R$^1$ being
a substituted biphenyl comprising at least one —CN as a substituent, particularly on the phenyl moiety not connected to the parent moiety, wherein in particular one phenyl moiety comprises additionally at least one —F as a substituent, more particularly each phenyl moiety comprises additionally at least one —F as a substituent,
R$^7$ being
an unsubstituted C$_1$-C$_6$ alcohol, in particular a C$_3$ alcohol, more particularly isopropanol,
in case of formula (5b")
R$^1$ being
an unsubstituted biphenyl,
a substituted biphenyl comprising at least one —CN as a substituent, particularly on the phenyl moiety not connected to the parent moiety, wherein in particular one phenyl moiety comprises additionally at least one —F as a substituent, more particularly each phenyl moiety comprises additionally at least one —F as a substituent,
wherein in particular R$^1$ being
a substituted biphenyl comprising at least one —CN as a substituent, particularly on the phenyl moiety not connected to the parent moiety, wherein in particular one phenyl moiety comprises additionally at least one —F as a substituent, more particularly each phenyl moiety comprises additionally at least one —F as a substituent,
R$^7$ being
an unsubstituted C$_1$-C$_6$ alcohol, in particular a C$_3$ alcohol, more particularly isopropanol,
R$^9$ being
a halogen, in particular —F.

In certain embodiments, the compound comprises the general formula (2a"), (3a"), (5a") or (5b"), as described above.

In certain embodiment, the compound comprises the general formula (5a"), as described above.

In certain embodiments, the compound is selected from the compounds depicted in FIG. 11, namely L-838417, TPA023 (MK-0777), TPA123, MRK-409(MK-0343), NS1 1394, Ocinaplon(DOV-273547), TPA023B, TP003, N-Desmethylclobazam, 1, 2, 3, 4 and 5, in particular L-838417, TPA023 (MK-0777), TPA123, MRK-409(MK-0343), NS1 1394, Ocinaplon(DOV-273547), TPA023B, TP003, N-Desmethylclobazam, 1, 2, 3, and 5.

In certain embodiments, the compound is selected from the compounds depicted in FIG. 11, namely L-838417, TPA023 (MK-0777), TPA123, MRK-409(MK-0343), NS1 1394, Ocinaplon(DOV-273547), TPA023B, TP003, 1, 2, 3 and 5.

In certain embodiments, the compound is selected from the compounds depicted in FIG. 11, namely L-838417, TPA023 (MK-0777), TPA123, MRK-409(MK-0343), NS1 1394, Ocinaplon(DOV-273547), TPA023B, TP003, insbesondere TPA023B.

In another aspect of the invention, a compound according to the first subaspect for use in preventing Serotonin-, Histamine-, Chloroquine-, Compound48/80 (CAS NO. 94724-12-6) and bile acid-induced itch is provided.

In certain embodiments, the compound is for use in preventing Serotonin-, Chloroquine-, Compound48/80 (CAS NO. 94724-12-6) and bile acid-induced itch.

In certain embodiments, the compound is for use in preventing Serotonin-induced itch.

In certain embodiments, a compound according to the first subaspect for use in the treatment of itch in an animal is provided.

In another aspect of the invention, a positive allosteric α2 or α3 GABA$_A$ receptor modulator for use in the treatment of itch is provided.

In another aspect of the invention, a positive allosteric α2 or α3 GABA$_A$ receptor modulator according to the first aspect of the invention for use in the treatment of itch is provided.

Wherever alternatives for single separable features such as, for example, a functional group, are laid out herein as "embodiments", it is to be understood that such alternatives may be combined freely to form discrete embodiments of the invention disclosed herein.

The invention is further illustrated by the following examples and figures, from which further embodiments and advantages can be drawn. These examples are meant to illustrate the invention but not to limit its scope.

SHORT DESCRIPTION OF THE FIGURES

Figure 1B:
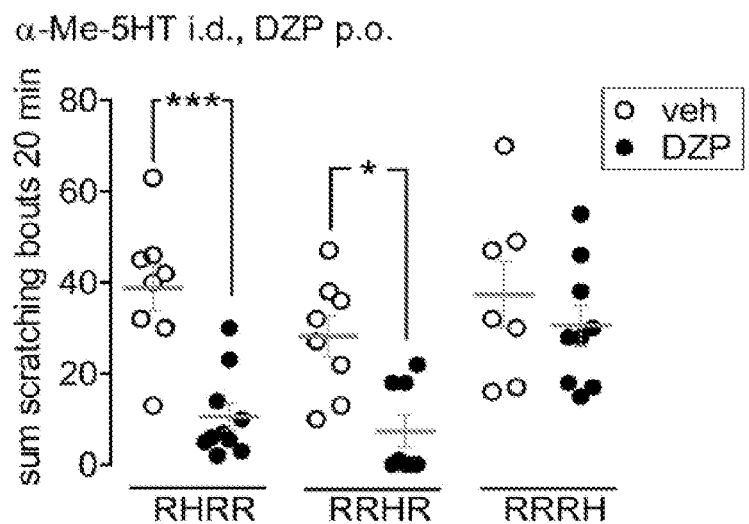

FIGS. 1A-1C show antipruritic effects by per oral diazepam (DZP in GABA$_A$R point-mutated mice of the 129X1/SvJ genetic background. DZP reduces number of scratching bouts elicited by cheek injection of 20 μg α-Me-5HT in GABA$_A$R triple point mutated mice, targeting α2, α3 or α5 in isolation. DZP was administered 1 h before α-Me-5HT injection. Time course (FIG. 1A): data points are mean±s.e.m., and statistical analysis of elicited scratching bouts directed at the ipsilateral cheek (FIG. 1B), quantified for 20 minutes. ***P<0.001;*P<0.05 versus vehicle treated mice (ANOVA followed by Bonferroni's post hoc test, F(5,44)=8.5). RHRR, RRHR, and RRRH mice are mice, in which all DZP-sensitive α subunits have been rendered DZP insensitive except for α2, α3, or α5, respectively. DZP insensitivity was introduced through histidine to arginine aminoacid exchanges at positions 101 for α1 and α2, 126 for α3, and 105 for α5. Number of mice (vehicle/DZP treated): RHRR n=8/10, RRHR n=8/8 and RRRH n=7/9, respectively. RHRR: α2 only, RRHR: α3 only, RRRH: α5 only.

Figure 2A:
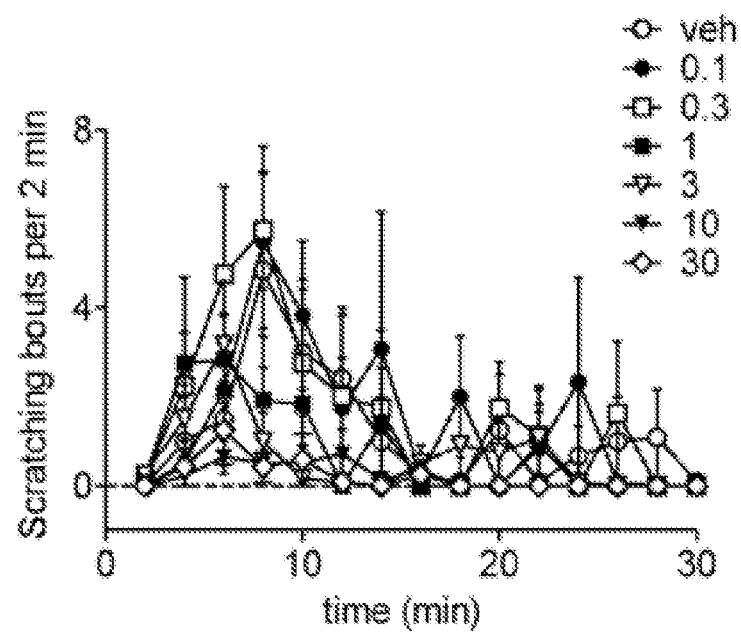
Figure 2B:
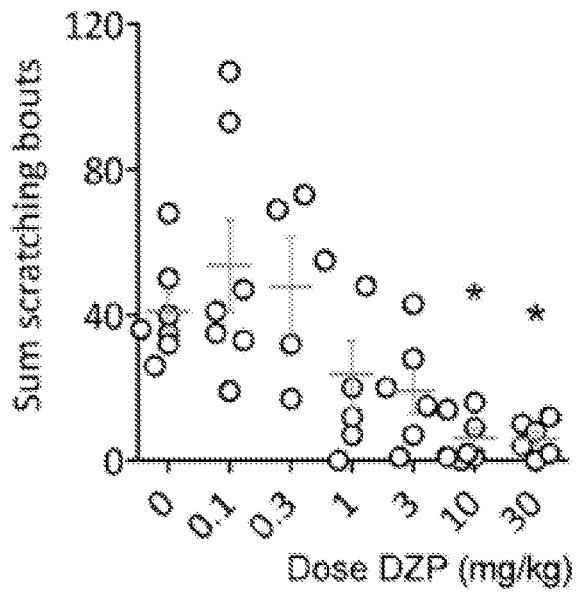
Figure 2C:
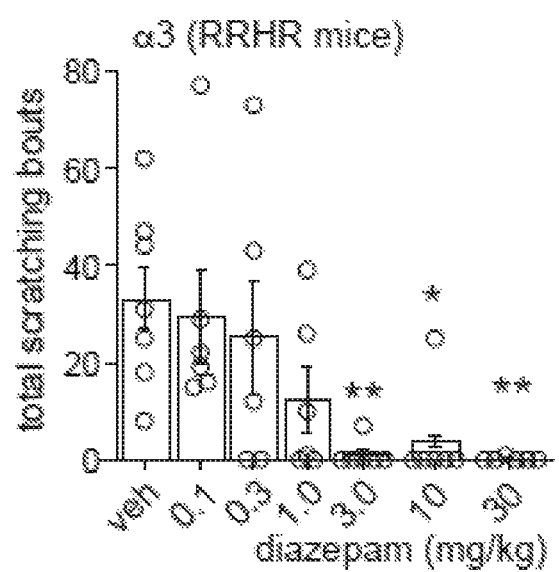

FIGS. 2A-2C show dose-dependent antipruritic effects of oral DZP against itch induced by intradermal injection of 20 μg α-Me-5HT in mice of the 129X1/SvJ genetic background. DZP was given 1 h before α-Me-5HT injection. (FIG. 2A) Time course data points are mean±s.e.m., and statistical analysis of elicited scratching bouts directed at the ipsilateral cheek quantified for 30 min; *P<0.05 versus vehicle treated mice (ANOVA followed by Dunnett's post hoc test, F(6, 37)=6. Number of mice: n=7, 7, 4, 6, 6, 7 and 6 for vehicle, 0.1, 0.3, 1, 3, 10 and 30 mg/kg, respectively. (FIG. 2B) dose-dependence of the antipruritic effects of diazepam in RHRR mice (only α2 GABA$_A$R$_S$ sensitive to diazepam). ANOVA followed by Dunnett's post hoc test F(6,36)=6.02; *, P<0.05; **, P<0.01, n=4-7 per group. (FIG. 2C) same as (FIG. 2B) but RRHR mice (only α3 GABA$_A$R$_S$ sensitive to diazepam). ANOVA followed by Dunnett's post hoc test F(6,37)=4.42; *, P<0.05; **, P<0.01, n=6-8 mice per group.

Figure 3A:
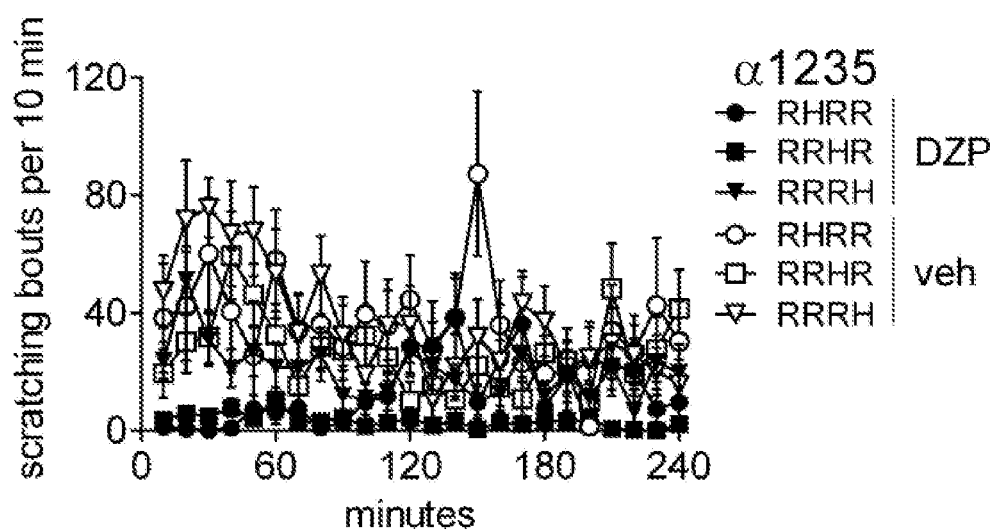
Figure 3B:
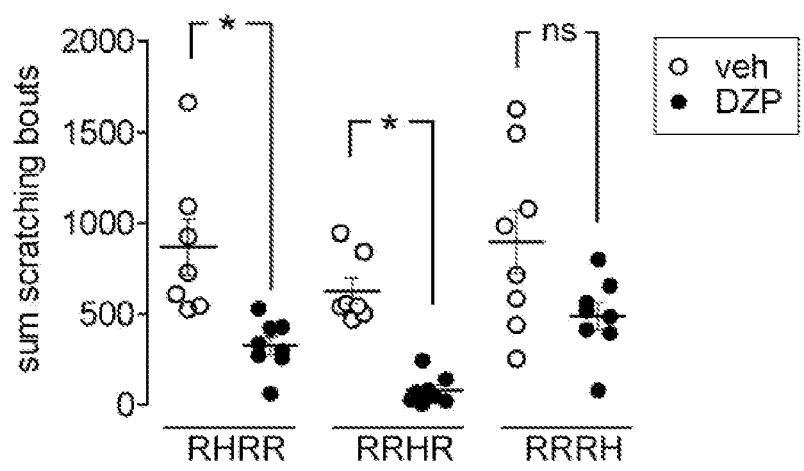
Figure 3C:
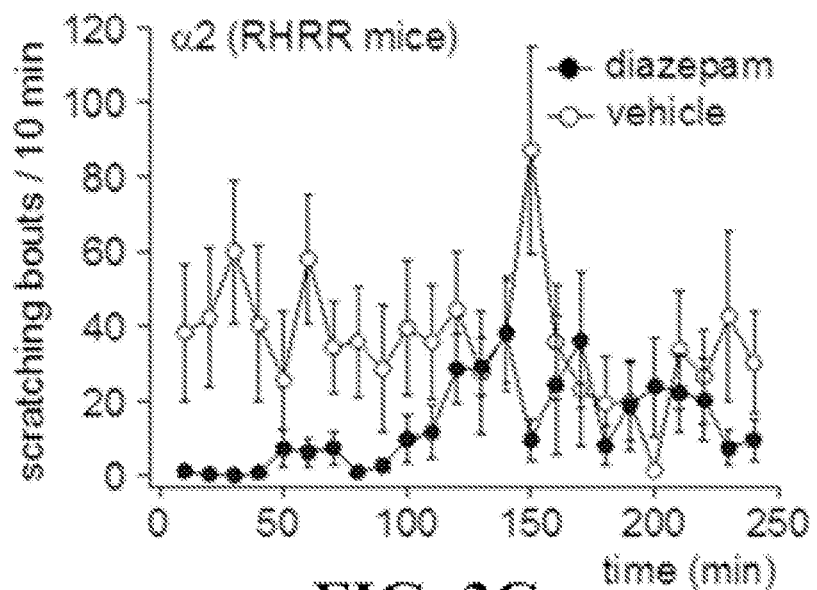
Figure 3D:
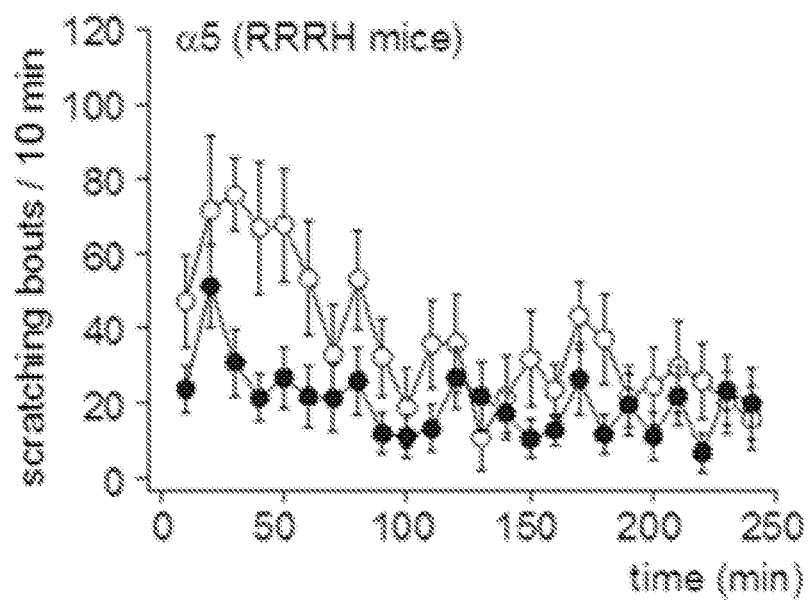
Figure 3E:
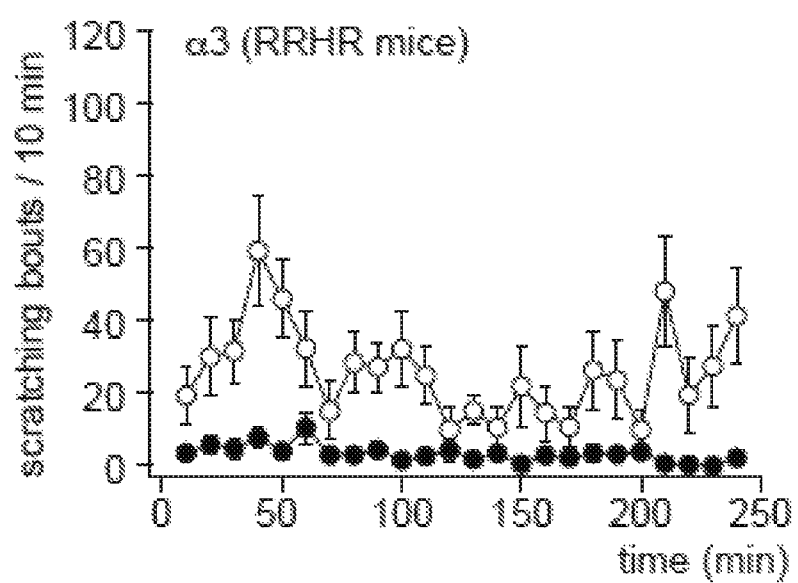

FIGS. 3A-3E show effects by per oral DZP in triple GABA$_A$R point-mutated mice of the 129X1/SvJ genetic background, assessed in a model of chronic contact dermatitis. RH RR, RRHR, and RRRH mice were treated with 100 μL 10% oxazolone (4-Ethoxymethylene-2-phenyl-2-oxazolin-5-one, Sigma) dissolved in acetone/olive oil (4:1) on day 1 to the nape of the neck, and with 100 μL 1% oxazolone on day 7-17 every other day to induce contact dermatitis and chronic itch. On day 18, mice were injected with 10 mg/kg DZP i.p. Time course (FIG. 3A) data points are mean±s.e.m., and statistical analysis (FIG. 3B) of number of scratching bouts between 0 and 240 min after directed to the nape of the neck; *P<0.05 versus vehicle treated mice (ANOVA followed by Bonferroni's post hoc test, F(3,35)=0.63. Number of mice (vehicle/DZP treated): RHRR n=6/7, RRHR n=6/7 and RRRH n=7/7 (FIG. 3C-FIG. 3E) Scratching bouts were counted for 6 hours starting 15 min after drug or vehicle administration. Number of scratching bouts plotted versus time after drug or vehicle administration in RHRR mice (e FIG. 3C), RRRH mice (FIG. 3D) and RRHR mice (FIG. 3E).

Figure 4A:
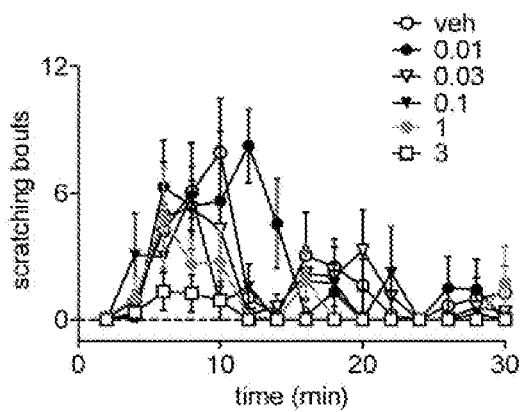
Figure 4B:
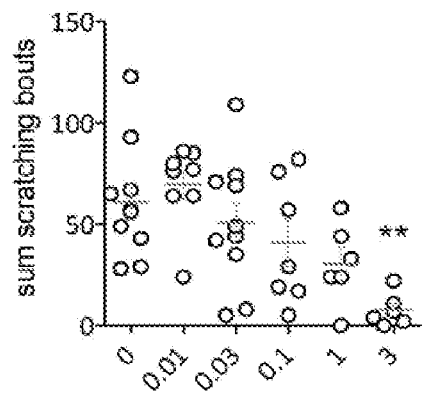
Figure 4C:
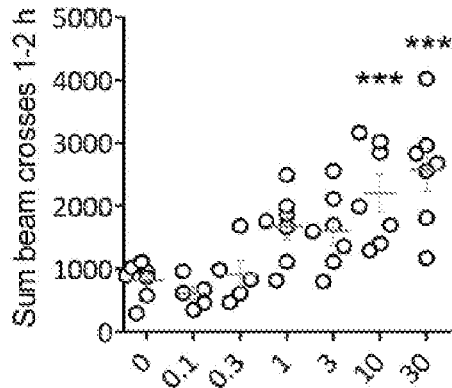

FIGS. 4A-4C show antipruritic effects of oral TPA023B against itch induced by intradermal injection of 100 μg histamine in wild-type C57BL6/J mice. Time course (FIG. 4A) data points are mean±s.e.m., and statistical analysis of elicited scratching bouts directed at the ipsilateral cheek (FIG. 4B), quantified for 30 minutes. P<0.01 versus vehicle treated mice (ANOVA followed by Dunnett's post hoc test, F(5, 42)=5.2. Number of mice: n=10, 8, 10, 7, 6, and 6 for vehicle, 0.01, 0.03, 0.1, 1 and 3 mg/kg, respectively. (FIG. 4C) absence of sedative effects of per oral TPA023B. TPA023B was injected immediately before the mouse was placed in the open field arena. *P<0.001 versus vehicle treated mice (ANOVA followed by Dunnett's post hoc test, F(5,34)=7.6). Number of mice: n=7, 5, 7, 7, 7 and 7 for vehicle, 0.3, 1, 3, 10 and 30 mg/kg, respectively. All data points are mean±s.e.m obtained between 1-2 h after injection.

Figure 5A:
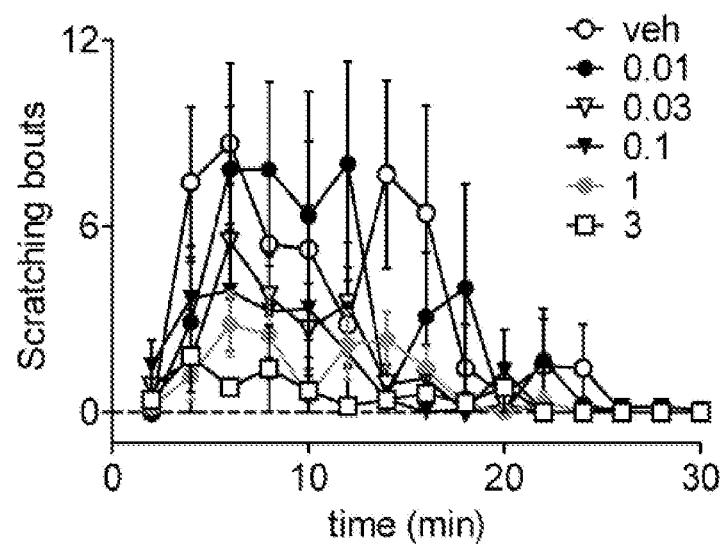
Figure 5B:
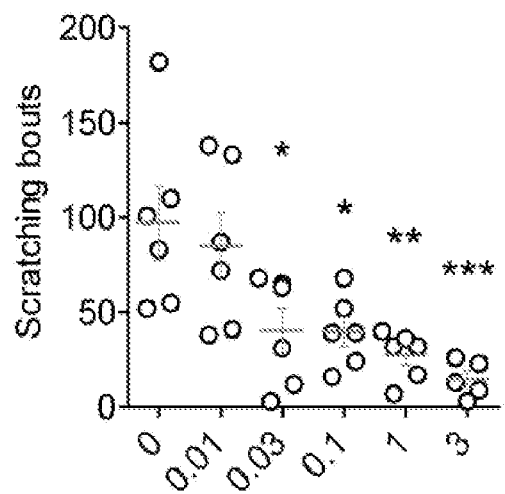

FIGS. 5A-5B show antipruritic effects of oral TPA023B dose against itch induced by intradermal injection of 100 μg chloroquine in wild-type C57BL6/J mice. Time course (FIG. 5A) data points are mean±s.e.m., and statistical analysis of elicited scratching bouts directed at the ipsilateral cheek (FIG. 5B), quantified for 30 minutes. *P<0.001; P<0.01; *P<0.05 versus vehicle treated mice (ANOVA followed by Dunnett's post hoc test, F(5, 30)=6.4. Number of mice: n=6, 6, 6, 6, 6, and 5 for vehicle, 0.01, 0.03, 0.1, 1 and 3 mg/kg, respectively.

Figure 6A:
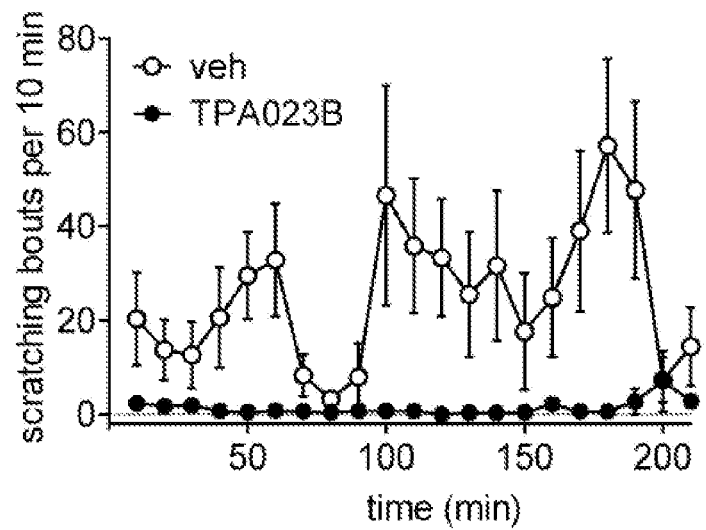
Figure 6B:
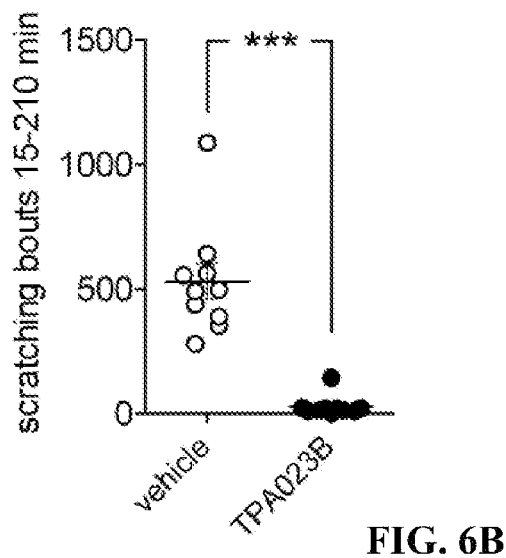

FIGS. 6A-6B show antipruritic efficacy of TPA023B in the contact dermatitis model of chronic itch. Wild-type C57BL6/J mice were treated with 100 μL 10% oxazol one (4-Ethoxymethylene-2-phenyl-2-oxazolin-5-one, Sigma) dissolved in acetone/olive oil (4:1) on day 1 to the nape of the neck, and with 100 μL 1% oxazolone on day 7-17 every other day. On day 18, mice were injected with 1 mg/kg TPA023B i.p. Time course (FIG. 6A) data points are mean±s.e.m., and statistical analysis (FIG. 6B) of number of scratching bouts directed to the nape of the neck, quantified between 15-210 min after injection. ***P<0.001 (unpaired t-test), n=10 for vehicle and TPA023B treated mice.

Figure 7A:
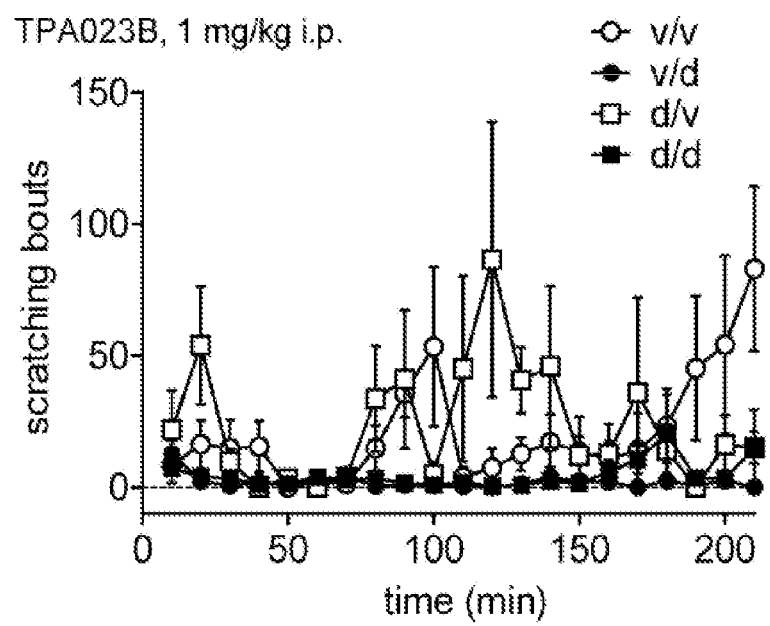
Figure 7B:
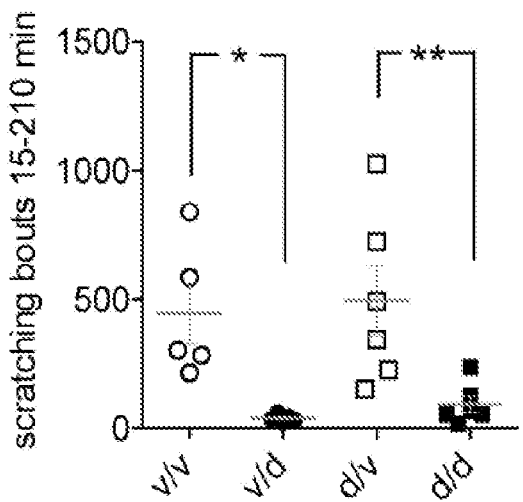

FIGS. 7A-7B show absence of tolerance development to the antipruritic effects of TPA023B in wild-type C57BL6/J mice. Mice were treated with 10% oxazolone on day 1, and 1% oxazolone on days 7-27. From day 17 onward, mice were treated with vehicle or 1 mg/kg TPA023B once daily for nine consecutive days. On day 28, mice were given either vehicle or TPA023B (1 mg/kg i.p.). Time course (FIG. 7A) data points are mean±s.e.m., and statistical analysis (FIG. 7B) of number of scratching bouts directed to the nape of the neck, quantified between 15-90 min after injection. *P<0.05; **P<0.01 (unpaired t-test). Twoway ANOVA for the interaction pretreatment*acute treatment F(3, 16)=1, n=5, 5, 6 and 6 for vehicle/vehicle (v/v), vehicle/TPA023B (v/d), TPA023B/vehicle (d/v) and TPA023B/TPA023B (d/d) treated mice, respectively.

Figure 8A:
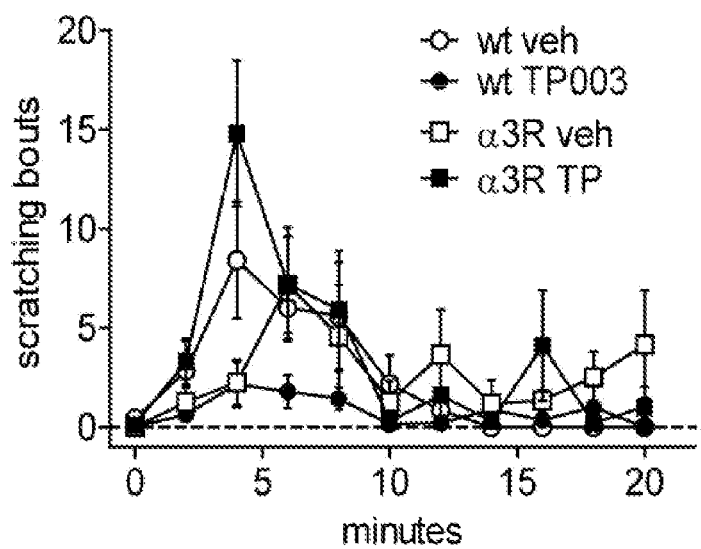
Figure 8B:
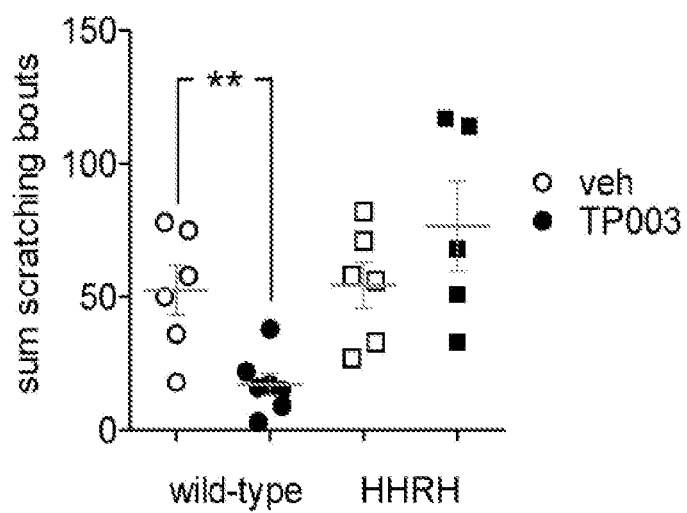

FIGS. 8A-8B show antipruritic effects of the α3-GABA$_A$ receptor selective compound TP003 (10 mg/kg, per oral) against 20 μg α-Me-5HT-induced itch in wild-type 129X1/SvJ mice, but not point mutated mice whose α3-GABA$_A$R had been rendered DZP-insensitive (HHRH mice). TP003 was injection 1 h before μg α-Me-5HT injection. Time course (FIG. 8A) data points are mean±s.e.m., and statistical analysis of elicited scratching bouts directed at the ipsilateral cheek (FIG. 8B), quantified for 20 minutes. **P<0.01 versus vehicle treated mice (unpaired ttest). Two-way ANOVA for the interaction pretreatment*acute treatment F(3,20)=8.7, n=6 and 7 for vehicle and TP003 treated wild-type mice, respectively, n=6 and 5 for vehicle and TP003 treated HHRH mice, respectively.

Figure 9A:
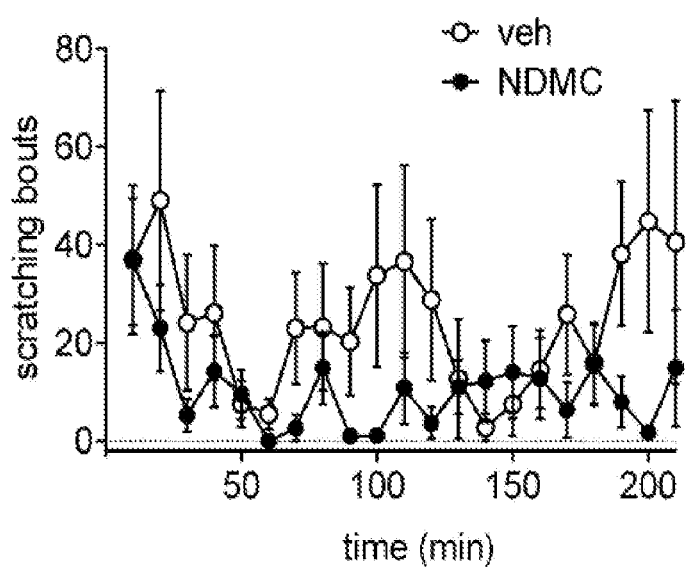
Figure 9B:
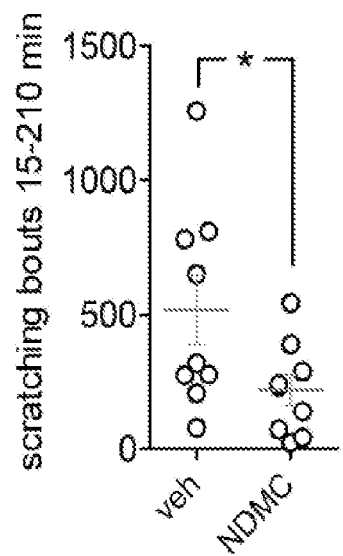

FIGS. 9A-9B show antipruritic effects of NDMC in the contact dermatitis model of chronic itch. Wild-type C57BL6/J mice were treated with 100 µL 10% oxazolone (4-Ethoxymethylene-2-phenyl-2-oxazolin-5-one, Sigma) dissolved in acetone/olive oil (4:1) on day 1 to the nape of the neck, and with 100 µL 1% oxazolone on day 7-17 every other day. On day 18, mice were injected with 10 mg/kg NDMC i.p. Time course (FIG. 9A) data points are mean±s.e.m., and statistical analysis (FIG. 9B) of number of scratching bouts directed to the nape of the neck, quantified between 15-210 min after injection. *P<0.05 (unpaired ttest), n=9 for vehicle and NDMC treated mice.

Figure 10A:
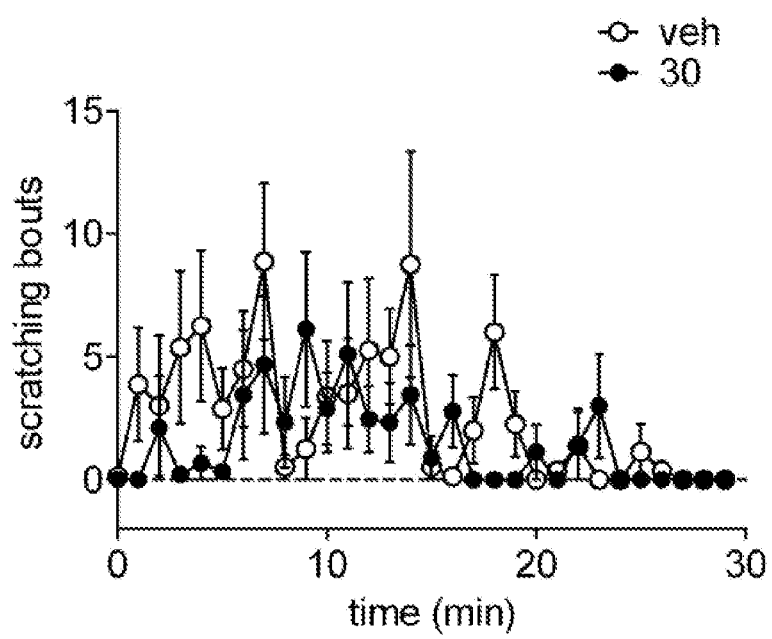
Figure 10B:
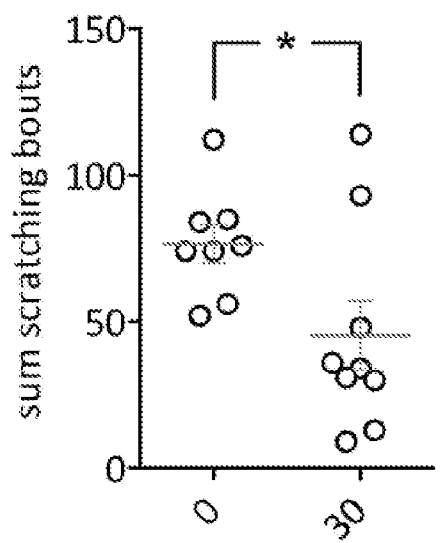

FIGS. 10A-10B show antipruritic effect of the neurosteroid ganaxolone injected intraperitoneally (30 mg/kg) against itch induced by intradermal injection of 100 µg chloroquine in in wild-type C57BL6/J mice. Time course (FIG. 10A) data points are mean±s.e.m., and statistical analysis of elicited scratching bouts directed at the ipsilateral cheek (FIG. 10B), quantified for 30 minutes. *P<0.05 versus vehicle treated mice (unpaired t-test). Number of mice: n=8 and 9 for vehicle and ganaxolone, respectively.

FIG. 11 shows structures of allosteric $GABA_A$ receptor modulators.

Figure 12A:
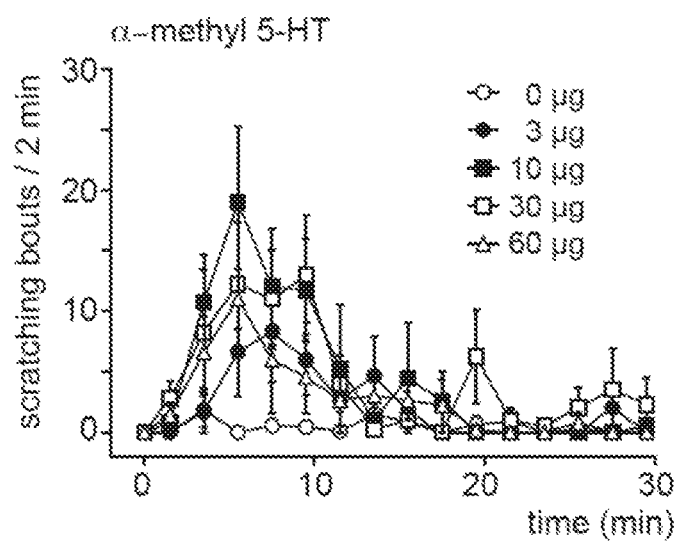
Figure 12B:
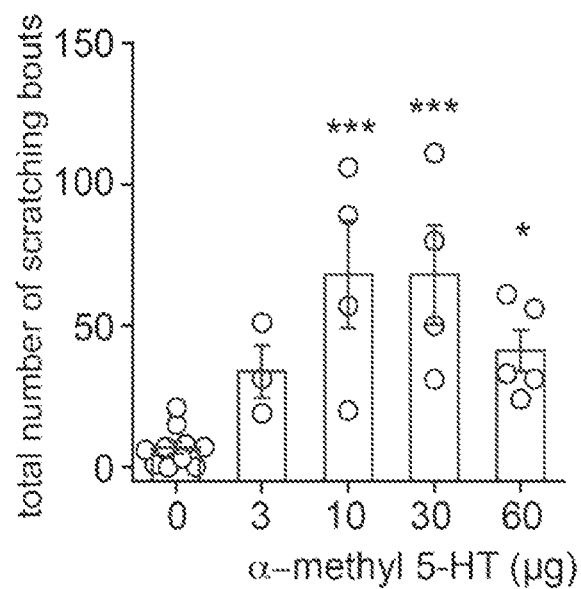

FIGS. 12A-12B show dose finding for a-methyl 5-HT in 129 SvJ mice. (A) Scratching responses in wild-type 129X1/SvJ evoked by the metabolically more stable serotonin analog a-methyl 5-HT. Different doses of a-methyl 5-HT were injected intracutaneously into the right cheek and scratching responses were counted for 30 min. (FIG. 12A) Number of scratching bouts (mean±SEM) over time following injection of a-methyl 5-HT. (FIG. 12B) Quantification and statistical analyses (ANOVA followed by Dunnett's post hoc test). Circles are values obtained from individual mice. Bars and error bars are means and SEM. F(4,21)=8.84; *, P<0.05; ***, P<0.001; n=3-10 per group.

Figure 13A:
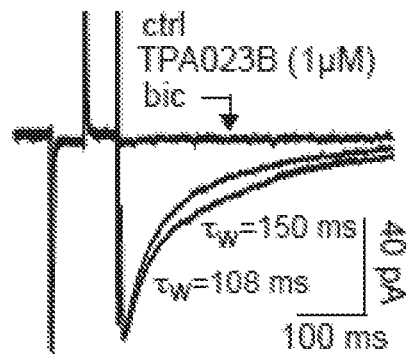
Figure 13B:
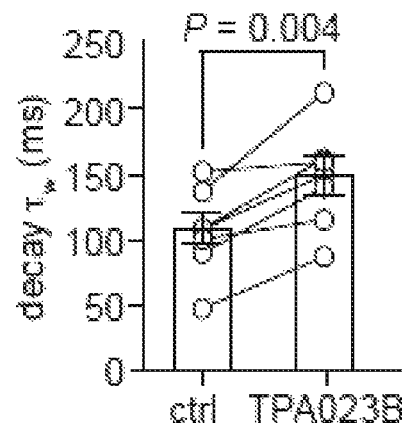
Figure 13C:
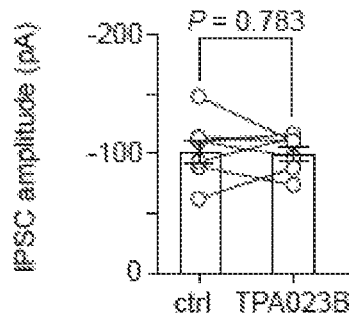

FIGS. 13A-13C show in vitro and in vivo pharmacological profile of TPA023B. (FIG. 13A) Examples of GABAergic IPSCs (averages of 10 consecutive current traces) recorded under control conditions (black), in the presence of TPA023B (µM, grey) and bicuculline (bic 10 µM, marked by an arrow). Superimposed in green are fits to double exponential functions. IPSCs were evoked by electrical field stimulation and preceded by hyperpolarizing voltage step to monitor access resistance and leak currents. Changes in the weighted time constant of IPSC decay (FIG. 13B) and amplitude (FIG. 13C). Circles are individual cells. Bars and error bars are mean±SEM. P values have been obtained from paired t-tests. n, number of cells was 7 for both analyses.

Figure 14:
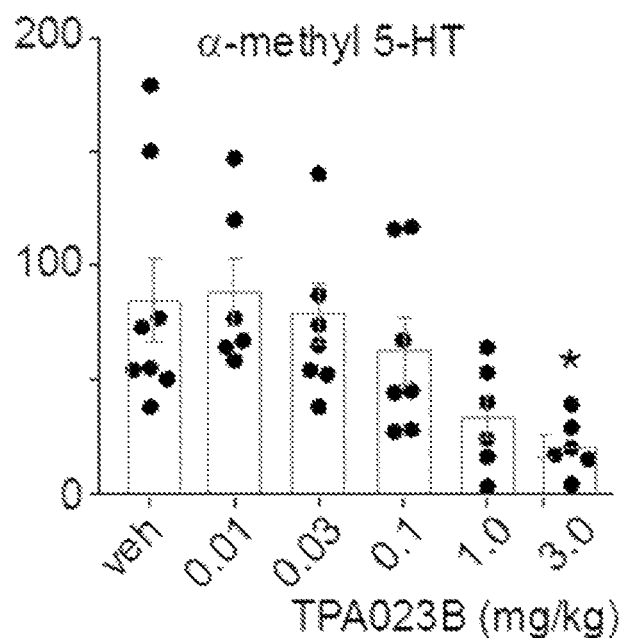

FIG. 14 shows antipruritic actions of TPA023B (p.o.) in mouse models of acute itch. Itch responses were induced by intracutaneous injection of α-Me5HT (20 µg) n=8, 6, 7, 7, 6, and 6 mice, for veh, 0.01, 0.03, 0.1, 1.0 and 3.0 mg/kg.

Figure 15:
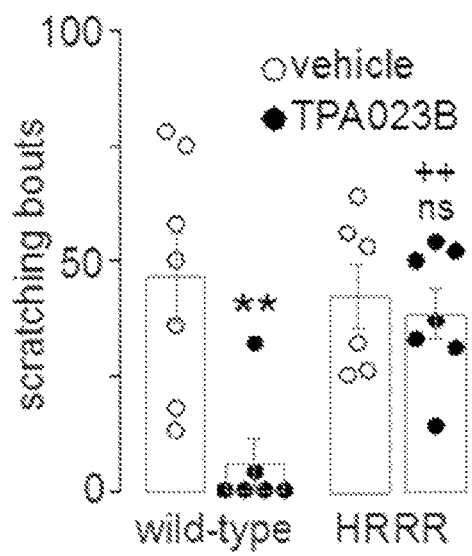

FIG. 15 shows that the antipruritic action of TPA023B occurs via the benzodiazepine bind site of GABAARs. α-methyl 5-HT (20 µg) was injected intracutaneously into the right cheek. TPA023B (1 mg/kg, p.o.) exerted strong antipruritic actions in wild-type mice. In HRRR mice, in which all TPA023B sensitive GABAARS subtypes had been rendered benzodiazepine-insensitive, TPA023B had completely lost its antipruritic action. Two-way ANOVA F(2, 22)=6.45. P=0.019 for genotype x treatment. P=0.005 (**) and 0.60 (ns) for treatment effect in wild-type and HRRR mice, respectively (n=6-7 mice per group). ++, P<0.01 relative to TPA023B-treated wild-type mice. (C) Antipruritic action of intrathecal injected TPA023B (0.3 mg/kg) in wild-type mice. Chloroquine (100 µg) was injected intracutaneously into the skin of the right thigh.

Figure 16A:
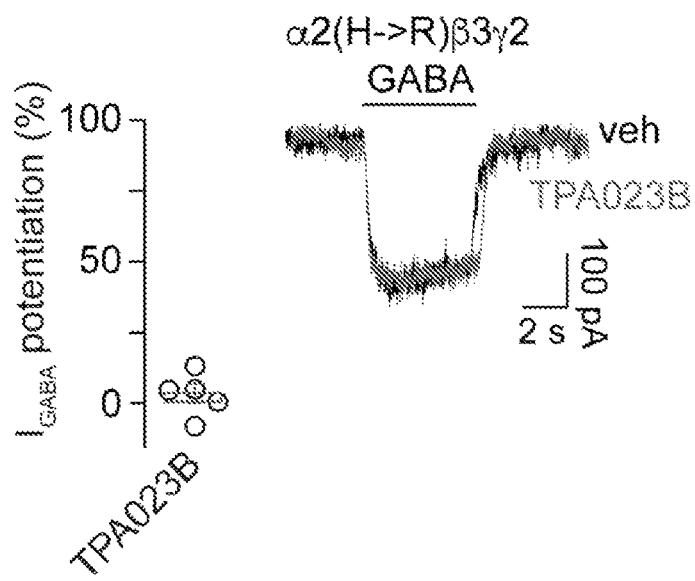
Figure 16B:
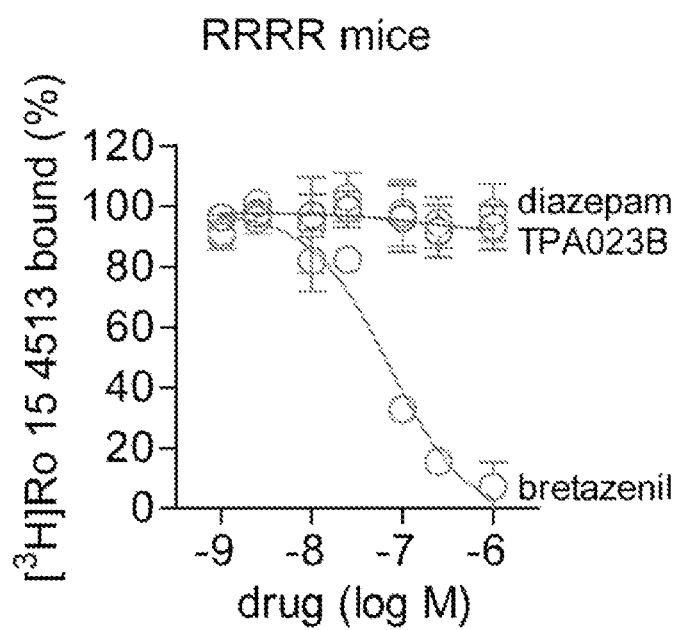

FIGS. 16A-16B show that the H→R point mutation in $GABA_A R$ α subunits prevents modulation and binding of $GABA_A R_S$ by TPA023B. (FIG. 16A) Positive allosteric modulation by TPA023B (1 µM) of a2$GABA_A R_S$ in HEK 293 cells is abolished by the H→R point mutation in the α2 subunit. (FIG. 16B) Accordingly, TPA023B failed to displace [$^3$H]Ro 15-4513 binding to brain membranes prepared from α1,2,3,5 H→R point mutated mice. The same was confirmed for diazepam, which only binds to α(H/H) receptors. In contrast, bretazenil which binds to both α(H/H) and α(R/R) receptors dose-dependently inhibited [$^3$H]Ro 15-4513 binding. Means±SD, n=4. Error bars smaller than the symbol are not visible.

Figure 17A:
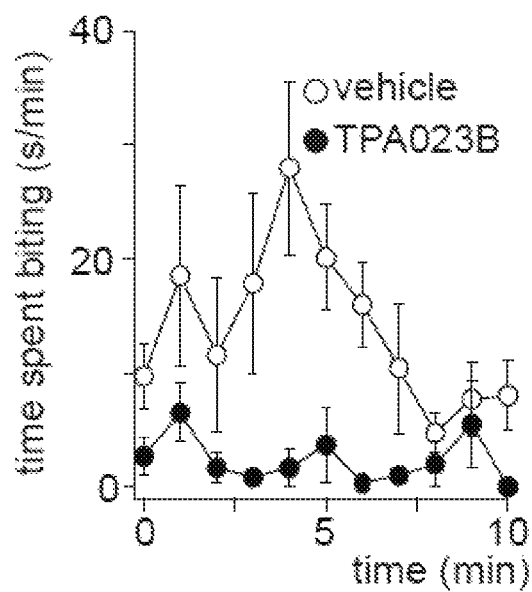
Figure 17B:
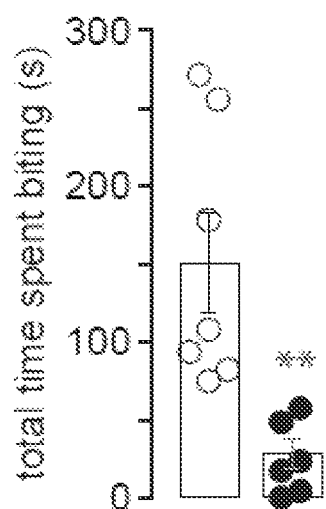
Figure 17C:
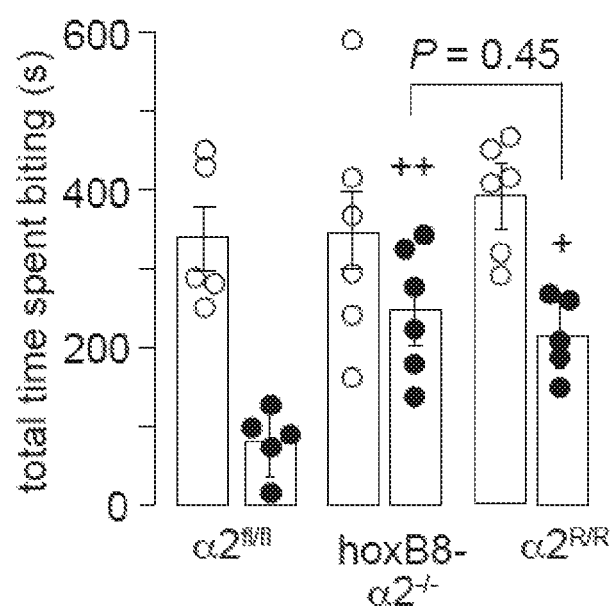

FIGS. 17A-17C show antipruritic action of intrathecally (i.e. into the spinal canal) injected TPA023B (0.3 mg/kg) in wild-type mice. Chloroquine (100 µg) was injected intracutaneously into the skin of the right thigh. (FIG. 17A) Time spent biting in the injected skin area (s/min). (FIG. 17B) Total number of scratching bouts counted during 0-10 min after pruritogen injection. P=0.008, unpaired t-test (n=6-7 mice). (FIG. 17C) Antipruritic action of TPA023B (1 mg/kg) in hoxB8-α2$^{-/-}$ mice lacking α2$GABA_A R_S$ specifically from the spinal cord. $GABA_A R$ α2$^{fl/fl}$ mice and global α2$GABA_A R$ (H→R) point mutated mice are shown for comparison. Chloroquine (100 µg) was injected intracutaneously into the right thigh. Chloroquine-induced biting responses (total time spent biting the injected skin area) were virtually identical in all three genotypes (ANOVA followed by Bonferroni post-hoc test F(14,2)=0.39, P=1.0 for all comparisons). By contrast, biting responses in TPA023B (1 mg/kg, p.o.) treated mice differed significantly between genotypes (ANOVA followed by Bonferroni post-hoc test F(2, 13)=10.6). +, P≤0.05; ++, P≤0.01. No significant difference (P=0.45) was found between hoxB8-α2$^{-/-}$ mice and global α2$^{R/R}$ mice indicating that at least the α2 $GABA_A R$-mediated component occurred through a spinal site.

EXAMPLES

Inhibitory neurons of the spinal dorsal horn release two fast amino acid transmitters, GABA and glycine, to reduce the excitability of their postsynaptic target neurons. In the present examples, the inventors focused their efforts on the GABAergic system and investigated whether itch, in particular chronic itch, can be suppressed by strengthening inhibition through pharmacological modulation of specific subtypes of spinal $GABA_A$ receptors ($GABA_A R_S$). $GABA_A R_S$ are anion channels built from a repertoire of 19 subunits. Most $GABA_A R_S$ in the brain and spinal cord are composed of α, β and γ subunits in a 2:2:1 stoichiometry. The mammalian genome harbors 12 genes encoding for these subunits (α1-6, β1-3 and γ1-3). Spinal $GABA_A R_S$ mainly contain α1, α2, α3, or α5 subunits together with β2/3 subunits and a γ subunit, while α4 and α6 subunits are only sparsely expressed or completely lacking. Differences in the physiological functions and pharmacological properties of these $GABA_A R_S$ are mainly determined by the α subunit. The inventors used genetically modified mice to identify α2/α3 containing $GABA_A R_S$ as key elements of spinal itch control. Building on this result the inventors assessed potential antipruritic actions of α2/α3 $GABA_A R_S$ selective compounds and showed that they not only reduced acute histamine-dependent and histamine-independent itch in mice but also chronic itch in mice and dogs without apparent side effects.

Example 1: Antipruritic Effect of Diazepam (DZP)

$GABA_A$ receptor triple point mutated mice bearing either a benzodiazepine sensitive a2, a3 or a5 $GABA_A$ receptor (Ralvenius et al., Nat Comm 6:6803, 2015) were used to test the effect of DZP on serotonin-induced itch. Because mice of this particular genetic background (129SvJ) have not yet been systematically analyzed in itch experiments, the inventors first assessed the sensitivity of these mice to a battery of pruritogens injected into the right cheek. The inventors found that injection of cx-methyl serotonin (a-methyl 5-HT), a metabolically more stable derivative of the pivotal itch messenger serotonin, induced dose-dependent robust scratching behavior directed to the injected site (FIG. 12). To test possible antipruritic effects evoked by activation of defined $GABA_A$ receptor subtypes, the mice received 10 mg/kg of DZP or vehicle by per oral administration. One hour after DZP injection the mice received 20 g of a-methyl-5-hydroxy-tryptamine (a-Me-5HT), a serotonin receptor agonist, by cheek injection to elicit itching. Over the course of 20 minutes, scratching bouts directed at the ipsilateral cheek were recorded and DZP injected mice compared with vehicle injected control mice (FIGS. 1A & 1B).

Mice with DZP-sensitive α2 or α3 $GABA_A$ receptors showed a significant reduction of scratching bouts in response to DZP treatment whereas mice with only DZP sensitive α5 $GABA_A$ receptors showed no significant reduction in scratching bouts after DZP treatment. A possible contribution of a α1 receptors to an antipruritic effect of DZP could not be investigated since a α1 receptors confer the sedative effect of benzodiazepines. The remaining a-sub-units α4 and α6 are DZOP insensitive and therefore are highly unlikely to contribute to antipruritic effects of DZP. In consequence the inventors demonstrate an antipruritic effect of the benzodiazepine, DZP against serotonin-induced itching, which is mediated by α2 and α3 $GABA_A$ receptors.

Example 2: Dose-Dependent Antipruritic Effect of DZP

Mice with only a2 $GABA_A$ receptors sensitive to DZP (RHRR mice) were per orally administered with vehicle, or 0.1, 0.3, 1, 3, 10 and 30 mg/kg DZP in order to establish a dose-response relationship against itch induced by 20 pg a-Me-5HT. Over the course of thirty minutes, scratching bouts directed at the a-Me-5HT injected cheek were recorded and DZP treated mice compared with vehicle treated control mice (FIGS. 2A & 2B). DZP or vehicle were injected one hour before a-Me-5HT. The inventors demonstrate a dose-dependent reduction of scratching bouts by DZP treatment and mediated by Q2 $GABA_a$ receptors.

Example 3: Antipruritic Effect of Diazepam in the Chronic Itch Model of Contact Dermatitis $GABA_A$ receptor triple point mutated mice bearing only DZP-sensitive a2, a3 or a5 $GABA_A$ receptors were treated with 100 μl 10% oxazolone (4-Ethoxymethylene-2-phenyl-2-oxazolin-5-one; Sigma Aldrich) dissolved in acetone (olive oil (4:1) on the nape of the neck. From day 7 to day 17 these mice were treated daily with 100 μl 1% oxazolone to induce contact dermatitis and chronic itch. On day 18 the mice received 10 mg/kg DZP or vehicle by intraperitoneal injection. The number of scratching bouts directed at the nape of the neck was recorded for 4 hours after injection (FIGS. 3A & 3B).

Mice receiving DZP showed a significant reduction in the number of scratching bouts compared to mice receiving only vehicle (FIG. 2b). This demonstrates that the antipruritic effect of DZP is conferred via α2 and α3 $GABA_A$ receptors and is also effective in a mouse model of chronic itch.

Example 4: Antipruritic Effect of TPA023B

The inventors investigated other subtype specific $GABA_A$ receptor modulators such as TPA023B (Russell et al. J Med Chem, 49(4):1 235-8, 2006) for their suitability as antipruritic substances to further support their finding that in principle all α2 and α3 $GABA_A$ receptor agonists are suitable antipruritic substances.

TPA023B is an a2, a3 and a5 agonist and an a1 antagonist was first assessed for its antipruritic effects against a cheek injection of 100 μg histamine in wild-type C57BL/6 mice (FIGS. 4A & 4B). The mice were injected with per oral TPA023B 90 minutes before histamine injection. Doses of TPA023B were vehicle, 0.01, 0.03, 0.1, 1 and 3 mg/kg. The inventors demonstrate a dose-dependent reduction of scratching bouts by TPA023B treatment against histaminergic itch, showing that TPA023B is antipruritic in wild-type mice.

In order to exclude any sedative effects TPA023B might have on mice, a dose-response experiment was included (FIG. 4c). The mice received per oral injections of TPA023B in varying doses vehicle, 0.3, 1, 3, 10 and 30 mg/kg). After injection, the mice were placed in an open field arena and their activity was recorded for one hour starting one hour after injection. Mice injected with a dose of 10 mg/kg and 30 mg/kg showed a significant increase in activity compared to mice that only received an injection of vehicle, excluding any sedative effects of TPA023B in wild-type mice.

A second pruritogen was included in order to confirm the antipruritic effect of TPA023B in wild-type animals, and to prove efficacy against non-histaminergic itch. The same doses as in FIGS. 4A-4C of TPA023B were injected 90 minutes before a cheek injection of 100 g chloroquine (FIGS. 5A & 5B). The inventors demonstrate a dose-dependent reduction of scratching bouts by TPA023B treatment against chloroquine-induced itch, confirming that TPA023B is antipruritic against non-histaminergic itch in wild-type mice. In order to assess the antipruritic effect of TPA023B in a clinically relevant disease, the contact dermatitis model of chronic itch was used. To this end, wild-type C57BL/6 mice were treated with 100 μl 10% oxazolone (4-Ethoxymethylene-2-phenyl-2-oxazolin-5-one; Sigma Aldrich) dissolved in acetone (olive oil (4:1) on the nape of the neck. From day 7 to day 17 these mice were treated daily with 100 μl 1% oxazolone to induce contact dermatitis and chronic itch. On day 18 the mice received intraperitoneal injection of 1 mg/kg TPA023B. The number of scratching bouts directed at the nape of the neck was recorded between 15 to 210 minutes after injection (FIG. 6a). The TPA023B injected mice showed a significant reduction in scratching bouts as compared to the vehicle injected mice (FIG. 6b). Thus, TPA023B is, in accordance with the other findings of the inventors, suitable as an antipruritic substance.

The development of a tolerance towards the antipruritic effect of TPA023B, after prolonged treatment, was again investigated in the contact dermatitis model of chronic itch. To this end, wild-type C57BL/6 mice were treated with 100 μl 10% oxazolone (4-Ethoxymethylene-2-phenyl-2-oxazolin-5-one; Sigma Aldrich) dissolved in acetone (olive oil (4:1) on the nape of the neck. From day 7 to day 27 these mice were treated every other day with 100 µl 1% oxazolone to induce and maintain contact dermatitis and chronic itch. From day 17 onward, mice were treated with intraperitoneal injection of vehicle or 1 mg/kg TPA023B for nine consecutive days. On day 28, mice were given either intraperitoneal injection of vehicle or TPA023B (1 mg/kg). The number of scratching bouts directed to the nape of the neck between 15 to 210 min after injection was recorded (FIG. 7a). Mice that received TPA023B injection on day 28 showed a significant reduction in scratching bouts compared to mice receiving vehicle injection. This was independent of the treatment they received from day 7 to day 27. Mice receiving TPA023B treatment (d/d) showed the same reduction as mice receiving vehicle from day 7 to day 27 and TPA023B on day 28 (v/d) as compared to mice receiving only vehicle (v/v) or mice receiving TPA023B from day 7 to day 27 and vehicle on day 28 (d/v) (FIG. 7b). Thus, the inventors exclude tolerance development to the antipruritic effects of TPA023B.

Example 5: Antipruritic Effect of TP003 on Serotonin-Induced Itching

The function of α3 $GABA_A$ receptors in the antipruritic effects of benzodiazepines was further addressed employing the α3 $GABA_A$ receptor subtype specific agonist TP003 (4,2'-difluoro-5'-[8-fluoro-7-(1-hydroxy-1-methylethyl)imidazo[1,2-a]pyridin-3-yl]biphenyl-2-carbonitrile; Dias et al., J Neurosci, 25(46):1 0682-1 0688; 2005).

Wild-type and $GABA_AR$ single point mutated mice in which only α3 is rendered DZP-insensitive (HHRH mice) received per oral injection of 10 mg/kg TP003 or vehicle. One hour after injection, the mice received a 20 ga-Me-5HT cheek injection to elicit itching. Over the course of twenty minutes scratching bouts directed at the ipsilateral cheek were recorded and TP003 injected mice compared with vehicle injected control mice (FIGS. 8A & 8B).

Wild-type mice receiving TP003 injection showed a significant reduction of scratching bouts compared to vehicle injected control mice in the HHRH mice, the antipruritic effect of TP003 was absent. Activation of the α3 $GABA_A$ receptor is therefore sufficient to produce an antipruritic effect after serotonin induced itching.

Example 6: Antipruritic Effect of NDMC Contact Dermatitis-Induced Itching

The inventors sought to confirm the antipruritic efficacy of α2 and α3 $GABA_A$ receptor agonists against contact dermatitis-induced chronic itch. To this end, N-desmethyl clobazam, a benzodiazepine with improved activity at α2 versus α1 was assessed for its antipruritic effects (Jensen et al. PLoS One. 2014 Feb. 12; 9(2):e88456.). Wild-type C57BL/6 mice were treated with 100 µl 10% oxazolone (4-Ethoxymethylene-2-phenyl-2-oxazolin-5-one; Sigma Aldrich) dissolved in acetone (olive oil (4:1) on the nape of the neck. From day 7 to day 17 these mice were treated daily with 100 µl 1% oxazolone to induce contact dermatitis and chronic itch. On day 18 the mice received intraperitoneal injection of 10 mg/kg NDMC. The number of scratching bouts directed at the nape of the neck was recorded between 15 to 210 minutes after injection (FIG. 9a). The NDMC injected mice showed a significant reduction in scratching bouts as compared to the vehicle injected mice (FIG. 9b).

Thus, NDMC is, in accordance with the results obtained with TPA023B in Example 4, also suitable as an antipruritic sub stance.

Example 7: Antipruritic Effect of the Neurosteroid Qanaxolone on Chloroquine-Induced Itching A class of molecules, separate from benzodiazepines, that potentiate the $GABA_A$ receptors are the neurosteroids, such as ganaxolone (Carter et al., J Pharmacol Exp Ther. 1997 March; 280(3): 1284-95). In order to confirm the $GABA_A$ receptor as a target for treatment of pruritus, the inventors pretreated wild-type C57BL/6J mice with 30 mg/kg intraperitoneal ganaxolone (FIGS. 10A & 10B). The ganaxolone injected animals showed a significant reduction in number scratching bouts as compared to vehicle-treated mice. These data show that potentiating the inhibitory effects of $GABA_A$ receptors, whether through benzodiazepine or neurosteroid treatment, is a feasible strategy for reducing itch.

Example 8: Inhibitory Input to Spinal Pruritoceptors onto $2^{nd}$ Order Itch Neurons The inventors verified that itch signal propagating GRP (gastrin releasing peptide) neurons receive input from local inhibitory interneurons. To this end, the inventors performed retrograde mono/transsynaptic rabies virus-based tracing experiments initiated from GRP neurons in GRP::cre transgenic mice. This retrograde tracing identified numerous inhibitory and excitatory neurons presynaptic to GRP neurons. Transverse sections of the injected dorsal horn section were analysed by immunofluorescent imaging. Cre positive GRP neurons infected with AAV.flex. RabG and secondary rabies virus infected neurons were visualized. Co-staining with Lmxl b and Pax2 revealed 39% excitatory and 45% inhibitory transsynaptically labelled neurons, respectively. 16% of transsynaptically infected neurons were neither stained with antibodies against Lmxl b nor Pax2, and remained unclassified. About half of the inhibitory neurons (48%) were located in laminae I/II of the dorsal horn, where the majority of inhibitory neurons are purely GABAergic. The other half (52%) resided in deeper layers (laminae III/IV), where most inhibitory neurons co-express glycine and GABA.

Example 9: $GABA_AR$ Subtypes Expressed on Primary Pruritoceptor Terminals and $2^{nd}$ Order Itch Neurons The inventors investigated the presence of α1, α2, α3, and α5$GABA_AR$ subunits on GRP neurons ($2^{nd}$ order pruritoceptors) and spinal axons and terminals of primary MrgprA3 positive pruritoceptors. Both GRP neurons and MrgprA3 fibers are concentrated in lamina II, which harbors α2 and/or α3$GABA_AR$ subunits at high density. To identify GRP positive neurons and MrgprA3 positive axons and terminals, the inventors used GRP::eGFP and MrgprA3:: cre-eGFP transgenic mice. Analysis of spinal cord sections prepared from these mice confirmed that the expression of α2 and α3$GABA_AR$ subunits overlapped with that of GRP neurons and MrgrpA3 positive terminals. By contrast, α1 and α5 $GABA_AR$ subunits were largely missing from lamina II but concentrated in the deep dorsal horn. Confocal analysis at higher magnifications further demonstrated that α2 and α3 $GABA_AR$ subunits were indeed expressed by MrgprA3 fibers and GRP neurons.

Example 10: Antipruritic Efficacy of an α2/α3 Selective GABA$_A$R Modulator

The inventors tested whether the data obtained in genetically modified mice would translate into therapeutic efficacy of GABA$_A$R subtype-selective compounds. To this end, the inventors tested the antipruritic efficacy of the a 1-sparing GABA$_A$R modulator TPA023B in wild-type mice. Before TPA023B was tested in itch models, its in vitro pharmacological profile was verified in HEK293 cells transiently transfected with different subtypes of GABA$_A$R$_S$. TPA023B had partial agonistic activity at the benzodiazepine binding site of α2β3γ2 and α3β3γ2 GABA$_A$R$_S$, but did not potentiate GABA-induced currents in α1β2γ2 GABA$_A$R$_S$ and had only very weak potentiating effects on α5β2γ2 GABA$_A$R$_S$. It did not activate GABA$_A$R$_S$ in the absence of GABA. This partial agonistic activity at the benzodiazepine binding site of α2 and α3 GABA$_A$R$_S$ translated into a facilitation of GABAergic inhibition in GRP neurons (FIG. 13). Whole-cell recordings performed in acutely prepared spinal cord slices of GRP::eGFP mice revealed that TPA023B (1 μM) significantly prolonged the decay of GABAergic inhibitory postsynaptic currents (GABA-IPSCs) in GRP neurons by 43±10% (P<0.01, paired t-test, n=7), but did not affect the amplitude of GABA-IPSCs.

Would this favorable in vitro profile of TPA023B translate into reduced propensity to side effects? Consistent with the lack of agonistic activity in α1 GABA$_A$R$_S$, TPA023B did not show sedative effects at doses up to 3 mg/kg (p.o.), but instead increased locomotor activity in the open field test at 1 and 3 mg/kg, likely reflecting the anxiolytic activity of α2 GABA$_A$R$_S$. TPA023B did not cause muscle relaxation in the horizontal wire test and did not reduce motor coordination in the rotarod assay.

The inventors then continued investigating the efficacy of systemic (p.o.) TPA023B against acute itch evoked by chloroquine (100μζ) and a-methyl 5-HT (20 g), two mediators of non-histaminergic itch, and by histamine (100 \ig) injected intracutaneously into the right cheek (FIG. 5b and FIG. 14). Chloroquine-induced scratching behavior was reduced by TPA023B in wild-type mice at doses ≥0.03 mg/kg. Similar effects were obtained for a-methyl 5-HT-induced and histamine-induced itch. To verify that the antipruritic effect of TPA023B was due to its effects on the benzodiazepine binding site of GABA$_A$R$_S$, the inventors assessed its effect in GABA$_A$R triple point mutated mice, in which all GABA$_A$R$_S$ susceptible to modulation by TPA023B (a.2, a.3, and a.5 GABA$_A$R$_S$) had been rendered benzodiazepine-insensitive (i.e. in HRRR mice). The antipruritic action of TPA023B was completely lost in these mice (FIG. 15). As a pre-requisite of these experiments the inventors also verified that the H→R point mutation in the a subunit prevented binding and potentiation of GABA$_A$R$_S$ by TPA023B (FIGS. 16A-16B). Subsequent experiments with intrathecal injection of TPA023B (0.3 mg/kg) at the level of the lumbar spinal cord in wild-type mice (FIGS. 17A-17C) and with systemic administration of TPA023B (3 mg/kg, p.o.) in hoxB8-GABA$_A$Rcx2" mice, which lack o2GABA$_A$R$_S$ specifically from the spinal cord, (FIGS. 17A-17C) confirm that the antipruritic action of TPA023B originates from the spinal cord or, in case of input from the facial skin, from the medullary dorsal horn.

Materials and Methods

Mice. Homozygous triple and quadruple (H→R) GABA$_A$R point-mutated mice were generated by cross breeding of single point-mutated mice described previously (Sun, Y. G., et al. *Science*, 2009, 325, 1531-1534; Ross, S. E., et al. *Neuron*, 2010, 65, 886-898; Rudolph, U. & Mohler, H. *Annu Rev Pharmacol Toxicol*, 2014, 54, 483-507). GABA$_A$R point mutated mice and the corresponding control mice were of the (129X1/SvJ) Background. Other transgenic mice (including single GABA$_A$R point mutated mice) and the corresponding control mice were of the C57BL/6 genetic background. BAC transgenic GRP::eGFP (Tg(Grp-EGFP) DV197Gsat/Mmucd) and GRP::cre (Tg(Grp-cre) KH288Gsat/Mmucd) were obtained from the GENSAT project (http://www.gensat.org), furthermore, BAC transgenic MrgprA3::cre-eGFP (Tg(Mrgpra3-GFP/cre)# Xzd) (Han, L, et al. *Nat Neurosci*, 2013, 16, 174-182) were used. These three BAC transgenic mouse lines were maintained in the heterozygous state. TVA reporter mice (Gt(ROSA) 26Sor<tml (Tva)Dsa) (Seidler, B., et al. *Proc Natl Acad Sci USA*, 2008, 105, 10137-10142) express the TVA transgene from a ubiquitous promoter in a cre dependent manner.

Drugs. Diazepam was obtained from Sigma. TPA023B (6,2'-difluoro-5'-[3-(1-hydroxy-1-methylethyl)imidazo[1,2-b][1,2,4]triazin-7-yl]biphenyl-2-carbonitrile) was synthesized by ANAWA, purity was >95%. For oral (p.o.) and intraperitoneal (i.p.) administration to mice, diazepam and TPA023B were suspended in 0.9% saline/1% Tween80. For electrophysiological experiments and radioligand binding, TPA023B was dissolved in DMSO and diluted with extracellular solution to 0.001-1 μM (final DMSO concentration ≤0.12%).

AAV preparation. AAV.flex.mCherry-2 A-RabG vector was cloned in-house and packaged at Penn Vector Core (Perelman School of Medicine, University of Pennsylvania) using their custom service. AAV.flex.mCherry-2A-RabG vector was cloned by excising the ChR2-mCherry fusion protein from pAAV-Efla-DIO-hChR2(H134R)-mCherry-WPRE-pA with Ascl and Nhel and replacing it with PGR amplified mCherry-2A-RabG cDNA. AAV of serotype 1 vector was used in this study.

Intraspinal virus injections. Animals were anesthetized with 2-5% isofluorane and lumbar vertebrae L4 and L5 were exposed. The animal was then placed in a motorized stereotaxic frame and the vertebral column was immobilized using a pair of spinal adaptors. The vertebral lamina and dorsal spinous process were removed to expose the L4 lumbar segment. The dura was perforated about 500 μm left of the dorsal blood vessel using a beveled 30G needle. Viral vectors were injected at a depth of 200-300 μm using a glass micropipette (tip diameter 30-40 μm) attached to a 10 μl Hamilton syringe. The rate of injection (30 nl/min) was controlled using a PHD Ultra syringe pump with a nanomite attachment (Harvard Apparatus, Holliston, Mass.). The micropipette was left in place for 5 min after the injection. Wounds were sutured and the animals were injected i.p. with 0.03 mg/kg buprenorphine and allowed to recover on a heat mat. Rabies virus injected mice were subjected to perfusion 3-5 days after injection.

Retrograde tracing experiments. Retrograde monosynaptic tracing experiments were initiated from GRP::cre expressing neurons of the lumbar spinal cord. A two-step strategy was used. This involved first an injection of an AAV helper virus (AAV.flex.mCherry-2A-RabG; 2.9×10$^9$ GC per injection in 300 nl) containing a bicistronic Cre-dependent mCherry and rabies glycoprotein (RbG) expression cassette, and fourteen days later a subsequent injection of an EnvA (avian sarcoma leukosis virus "A" envelop glycoprotein) pseudotyped glycoprotein-deficient rabies virus (EnvA.RabiesAG.eGFP; 1×10$^6$ GC per injection in 500 nl). The TVA protein expressed from the Rosa26 reporter mouse line (Seidler, B., et al. *Proc Natl Acad Sci USA*, 2008, 105, 10137-10142) enabled cell type specific infection of Grp::Cre+ neurons, and the RbG was expressed to transcomplement the glycoprotein-deficient rabies virus in primary infected neurons. For subsequent neurochemical analyses, mice were perfused with 4% paraformaldehyde (PFA) in PBS followed by postfixation in 4% PFA in PBS for 1-2 hours five days after rabies virus injection. The tissue was cut into 25 μm thick coronal cryosections, which were mounted onto Superfrost Plus microscope slides (Thermo Scientific, Zurich, Switzerland). The following antibodies were used: rat anti-mCherry (1:1000), rabbit anti-GFP (1:1000), chicken anti-GFP (1:1000), guinea pig anti-Lmx1b (1:10,000; gift from Carmen Birchmeier) rabbit anti Pax2 (1:400) and cyanine 3 (Cy3)-, Alexa Fluor 488-, DyLight 488-, 647- and 649-conjugated donkey secondary antibodies (1:500; Dianova, Hamburg, Germany).

Image analysis. Fluorescent images were acquired on a Zeiss LSM710 Pascal confocal microscope using a 0.8 NA 20× Plan-apochromat objective or a 1.3 NA 63× EC Plan-Neofluar oil-immersion objective and the ZEN2012 software (Carl Zeiss). Whenever applicable, contrast, illumination, and false colors were adjusted in ImageJ or Adobe Photoshop (Adobe Systems, Dublin, Ireland). Cell numbers were quantified in sections prepared from 4-8 animals and at least four sections were analyzed per animal. In order to avoid double counting of cells in adjacent sections, all sections used for quantification were taken at a distance of at least 50 μm. The numbers of immune reactive cells were determined using the ImageJ Cell Counter plug-in.

Immunohistochemistry and image analysis of $GABA_AR$ subunits. Colocalization of $GABA_AR$ a subunits with Mrg-prA3 terminals and GRP neurons was visualized on 40 μm thick horizontal mouse lumbar spinal cord cryosections. Mice were deeply anaesthetized with pentobarbital (nembutal, 50 mg/kg, i.p.) and perfused with oxygenated aCSF. Spinal cords were rapidly collected by pressure ejection and placed in ice-cold 4% PFA for 90 min. The spinal cords were then cryoprotected overnight in a 30% sucrose/PBS solution, snap frozen with dry ice and cut in 40 μm thick coronal free-floating slices kept in antifreeze at −20° C. until the day of staining (Seidler, B., et al. *Proc Natl Acad Sci USA,* 2008, 105, 10137-10142 (2008). Antibodies were home-made subunit-specific antisera (Seidler, B., et al. *Proc Natl Acad Sci USA,* 2008, 105, 10137-10142 (2008). Final dilutions were 1:20,000 (α1), 1:1,000 (α2), 1:10,000 (α3), and 1:3,000 (α5). The distribution of $GABA_AR$ a subunits in dorsal horn GRP neurons was analyzed by immunofluorescence staining on coronal sections prepared from 2-3 male GRP::eGFP transgenic mice as described above. For staining, the sections were incubated overnight at 4° C. with a mixture of primary antibodies diluted in Tris buffer containing 2% normal goat serum. Sections were washed extensively and incubated for 1 hour at room temperature with the corresponding secondary antibodies conjugated to Cy3 (1:500), Cy5 (1:200) (Jackson ImmunoResearch) or Alexa488 (1:1000, Molecular Probes, Eugene, Oreg.). Sections were washed again and cover-slipped with fluorescence mounting medium (DAKO, Carpinteria, Calif.).

Image acquisition and analysis was performed as described previously 'Paul, J., Zeilhofer, H. U. & Fritschy, J. M. *J Comp Neurol,* 2012, 520, 3895-391 1). Double-immunofluorescence signals were visualized by confocal microscopy (LSM 710; Zeiss AG, Jena, Germany) using a 63× Plan-Apochromat objective (N.A. 1.4). The pinhole was set to 1 Airy unit for each channel and separate color channels were acquired sequentially. The acquisition settings were adjusted to cover the entire dynamic range of the photomultipliers. Typically, stacks of confocal images (1024×1024 μlxels) spaced by 0.3 μm were acquired at a magnification of 56-130 nm/pixel. For display, images were processed with the image analysis software Imaris (Bitplane; Zurich, Switzerland). Images from all channels were overlaid (maximal intensity projection) and background was subtracted, when necessary. A low-pass filter was used for images displaying a subunit staining. Analysis of the distribution of a subunit-IR in GRP::eGFP neurons and dendrites was performed in single confocal sections from 2-3 mice acquired at a magnification of 78 nm/pixel in 8-bit gray scale images, using a threshold segmentation algorithm (minimal intensity, 90-130; area >0.08 nm$^2$).

Skin histology and immunofluorescence. Inflamed and healthy back skin was collected. Tissues were embedded in OCT compound (Sakura Finetek, Torrance, USA) and frozen on dry ice. Cryostat sections (7 μm) were placed on glass slides, air dried, fixed with acetone for 2 min at −20° C. and subsequently rehydrated with 80% methanol for 5 min at 4° C. Specimens were incubated with 5% donkey serum, 0.1% Triton-X and 1% BSA in PBS for 1 hour at room temperature, followed by overnight incubation with rat anti-mouse CD68 (1:200; Abeam, Cambridge, United Kingdom) at 4° C. The samples were incubated with Alexa Fluor 488- or 594-coupled secondary antibodies and Hoechst 33342 (all from Invitrogen, Life Technologies, Carlsbad, USA) for 30 min at room temperature. CD68-stained sections were examined on an Axioskop 2 mot plus microscope (Carl Zeiss, Feldbach, Switzerland), equipped with an AxioCam MRc camera (Zeiss) and a Plan-Apochromat 0.45 NA 10× objective (Zeiss). Images of at least four individual fields of view were acquired per section using Axio-Vision software 4.8. Using ImageJ v 1.49, the fluorescent area was determined between the stratum corneum and an outline thereof shifted 300 nm into the tissue. Results are expressed as CD68-positive area (nm$^2$) per nm basement membrane.

Electrophysiological recordings in HEK293 cells recordings. The effects of TPA023B on currents through recombinant $GABA_AR_S$ were studied in HEK293 cells (ATCC) transiently expressing $GABA_AR_S$. HEK293 cells were transfected using lipofectamine LTX (Dugue, G. P., et al. *Neuron,* 2009, 61, 126-139). To ensure expression of the γ2 subunit (required for modulation of $GABA_AR_S$ by BDZs) in all recorded cells, the inventors transfected cells with a plasmid expressing the γ2 subunit plus eGFP from an IRES, and only selected eGFP-positive cells for recordings. The transfection mixture contained (in μg): 1 α1, 1 β2, 3 γ2/eGFP (used as a marker of successful transfection) or 1 αx, 1 β3, 3 γ2/eGFP in case of α2, α3, or α5$GABA_AR_S$. Recordings were made 18-36 hrs after transfection. Whole-cell patch-clamp recordings of GABA-evoked currents were made at room temperature (20-24° C.) and at a holding potential of −60 mV. Recording electrodes were filled with solution containing (in mM): 120 CsCl, 10 EGTA, 10 HEPES (pH 7.40), 4 MgCl$_2$, 0.5 GTP and 2 ATP. The external solution contained (in mM): 150 NaCl, 10 KCl, 2.0 CaCl$_2$), 1.0 MgCl$_2$, 10 HEPES (pH 7.4), and 10 glucose. GABA was applied to the recorded cell using a manually controlled pulse (4-6 s) of a low sub-saturating GABA concentration (EC$_5$). EC$_5$ values of GABA were determined for all subunit combinations analyzed. EC$_{50}$ values and Hill coefficients (nn) were obtained from fits of normalized concentration-response curves to the equation $I_{GA}^{BA}=I_{max} [GABA]^{nH}/([GABA]^{nH}+[EC_{50}]^{nH})$. $I_{max}$ was determined as the average maximal current elicited by a concentration of 1 mM GABA. TPA023B was dissolved in DMSO and subsequently diluted with recording solution was co-applied together with GABA without pre-incubation.

Electrophysiological recordings in spinal cord slices. Transverse spinal cord slices (400 μm thick) were prepared from 20 to 29-day old GRP::eGFP mice of either sex as described previously (Dugue, G. P., et al. *Neuron,* 2009, 61, 126-139). Whole-cell patch clamp recordings were made at room temperature targeting eGFP positive neurons. During recordings, slices were continuously superfused at the rate of 1-2 ml/min with aSCF containing (in mM): 120 NaCl, 2.5 KCl, 1.25 $NaH_2PO_4$, 26 $NaH_2CO_3$, 5 HEPES, 1 $MgCl_2$, 2 $CaCl_2$) and 14.6 glucose (pH 7.4), equilibrated with 95% 02, 5% $CO_2$. Recorded neurons were voltage clamped at −70 mV using an EPC 9 amplifier (HEKA Elektronic, Lambrecht, Germany) controlled with Patchmaster acquisition software. Patch pipettes (borosilicate glass; 3.5-4.5 MS2) were filled with intracellular solution containing (in mM): 120 CsCl, 2 $MgCl_2$, 6 $H_2O$, 10 HEPES, 0.05 EGTA, 2 MgATP, 0.1 NaGTP, 5 QX-314 (pH 7.35). IPSCs were evoked by electrical stimulation (300 μs, 0.2-50 V) at 0.05 Hz using glass electrode filled with aCSF and placed 50-100 μm from the soma of the recorded cell. Experiments were performed in the presence of NBQX (20 μM), APS (50 μM) and strychnine (0.5 μM), in order to isolate the GABAergic component of IPSCs. At the end of the recordings bicuculline (10 μM) was added to confirm the GABAergic nature of the recorded IPCSs. The weighted decay time constant ($T_w$) was calculated from dual-exponential fits using the following equation: $T_W=(T_1A_1+T_2A_2)/(A_1+A_2)$ where $T_1$ and $T_2$ are the fast and the slow decay time constants and $A_1$ and $A_2$ are the equivalent amplitude weighting factors (Labrakakis, C, Lorenzo, L. E., Bories, C., Ribeiro-da-Silva, A. & De Koninck, *Y Mol Pain,* 2009, 5, 24). Access resistance of each neuron was continuously monitored with short hyperpolarizing voltage step applied before the electrical stimulation. Cells in which the access resistance changed more than 20% were excluded from the analysis.

$[^3H]_{Ro}$ 15-4513 binding. Brain tissue from 8-10 week old quadruple RRRR (H→R) point mutated mice, in which all high-affinity diazepam-sensitive binding were inactivated, was homogenized in 20 volumes of 10 mM Tris-HCl, pH 7.4, 100 mM KCl containing protease inhibitors (Complete Mini, Roche Diagnostics) and centrifuged at 1000 g for 10 min. The supernatant was centrifuged for 20 min at 30,000 g and the resulting crude membrane pellet was washed once with buffer. For radioligand binding, aliquots of the crude membranes (100 μg) were incubated with increasing concentrations of diazepam (binds to diazepam-sensitive sites), bretazenil (binds to diazepam-sensitive and insensitive sites; ref 48) or TPA023B and 4 nM [$^3H$]Ro 15-4513 (22.7 Ci/mmol, PerkinElmer, binds to diazepam-sensitive and insensitive sites) in a total volume of 0.2 ml for 90 min on ice. Non-specific [$^3H$]Ro 15-4513 binding was assessed by addition of 10 μM flumazenil to the reaction. Incubation was stopped by rapid vacuum filtration using a semiautomatic cell harvester (Skatron Instruments) and washed filters were subjected to liquid scintillation counting.

Behavioral experiments in mice. All behavioral experiments were performed in 7-12 week old female and male mice. Care was taken to ensure equal numbers of female and male mice. All behavioral experiments were made by a male experimenter, blinded either to the genotype of the mice or to their treatment with drug or vehicle. In experiments involving comparisons between diazepam or TPA023B and vehicle, mice were randomly assigned to the different groups.

Acute itch was assessed in mice that received intradermal microinjections of pruritogens or 0.9% saline into the right cheek, which had been shaved at least one day before the experiment. In two sets of experiments that addressed the contribution of $GABA_AR_S$ in primary and secondary pruritoceptors, pruritogens were injected in the right thigh (FIG. 17). Before injection, mice were acclimatized to a 15 cm diameter cylindrical enclosure for more than 30 min with cage bedding on the ground. Background white noise generated by a radio in the room at ambient volume was applied to prevent auditory distraction. A 30 gauge needle was inserted bevel-up and pushed 5 mm horizontally into the skin beyond the point of insertion, before injection of the pruritogen (in a total volume of 10 μl). No anesthesia was used. Correct injection was confirmed by the appearance of a slightly domed bulla upon injection. After injection, mice were placed back into the cylindrical enclosure and videotaped for 30 min. Videos were analyzed off-line. Scratching of the hind paw directed to the ipsilateral cheek was counted in bouts, with one scratching bout defined as an instance when the mouse lifted its paw to scratch until it returned the paw to the cage floor. In case of experiments in which the pruritogen was injected in the skin of the thigh, the time spent biting the injected skin area was counted in s/min as a measure of itch.

Chronic itch was investigated in the contact dermatitis model (Kido-Nakahara, M. et al. *J Clin Invest,* 2014, 124, 2683-2695). Mice were treated once with 10% oxazolone in acetone/olive oil (4:1 v/v) on the shaved nape of the neck (100 μl) on day 0. After a resting period of 7 days, mice were treated with 1% oxazolone in acetone/olive oil (4:1 v/v) on the nape of the neck (100 μl) every other day for 10 days. On the day of the experiment, mice were injected with drug or vehicle i.p. under short and light isoflurane anesthesia. Scratching of the hind paw directed to the ipsilateral cheek was quantified as the number of scratching bouts.

Locomotor activity, muscle relaxant effects and motor coordination were assessed as described previously (Ralvenius, W. T., Benke, D., Acuna, M. A., Rudolph, U. & Zeilhofer, H.U. *Nature Communications,* 2015, 6). In brief, TPA023B (1 mg/kg, p.o.) or vehicle was administered 60 min before the tests. Locomotor activity was analyzed for the time interval between 60 and 120 min after TPA023B administration. Motor coordination was assessed with a rotarod accelerating from 4 rpm to 40 rpm within 5 min. Sixty min after TPA023B administration, mice were placed onto the rotarod. Fifteen measurements were taken per mouse. To assess muscle relaxation, mice were placed with their forepaws onto a metal horizontal wire placed 20 cm above ground. Successes and failures to grab the wire with at least one hindpaw were recorded between 60 and 120 min after TPA023B administration.

The invention claimed is:

1. A method of treating itch in a subject comprising administering to the subject an amount of a compound selected from the group consisting of:

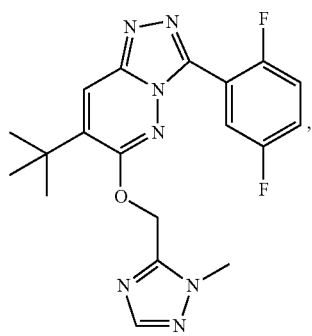

,

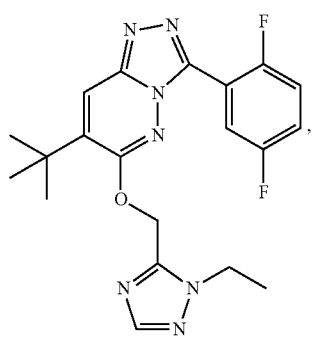

,

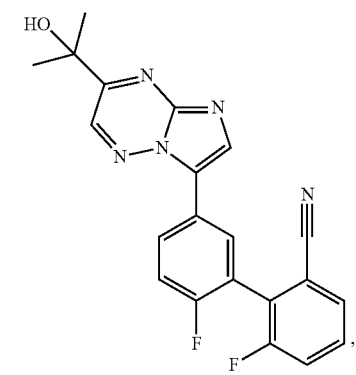

,

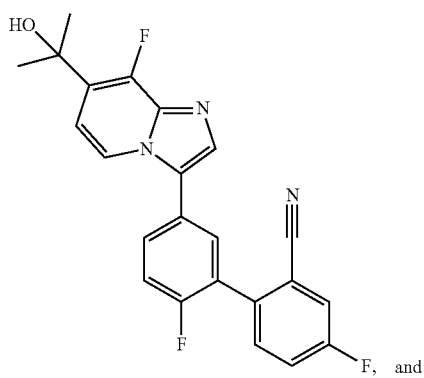

, and

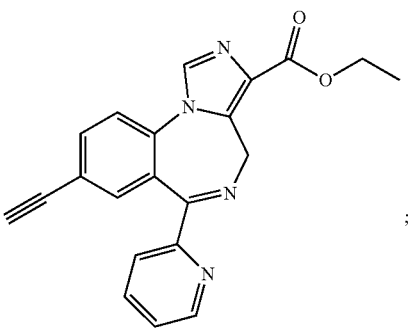

;

wherein the itch is not treatable with an antihistamine.

2. The method of claim 1, wherein the itch is associated with kidney disease, liver disease, or treatment with opioids.

3. The method of claim 1, wherein the compound is:

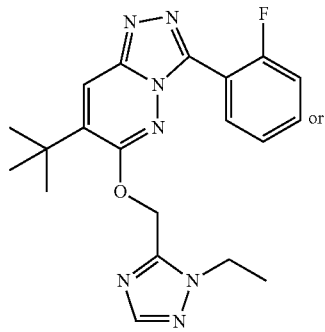

or

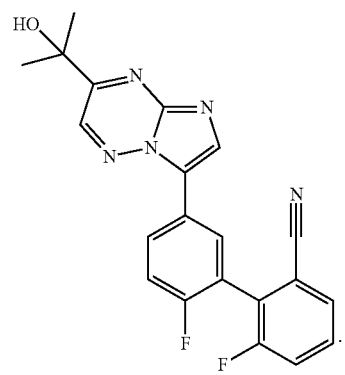

.

4. The method of claim 1, wherein the amount is effective to treat the histamine-independent itch when administered at a dose of from about 0.1 mg/kg per day to about 10 mg/kg per day of a body weight of a dog when administered to the dog.

5. A pharmaceutical composition comprising a compound selected from the group consisting of:
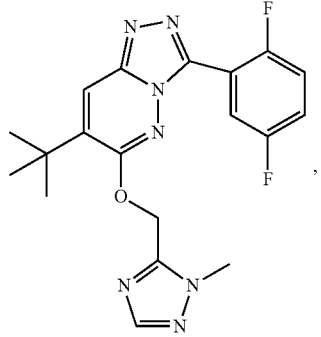
,
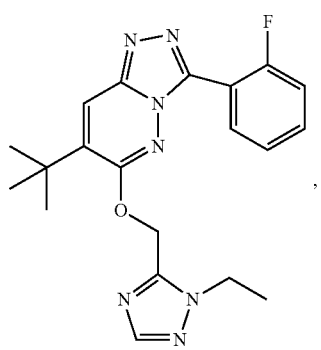
,
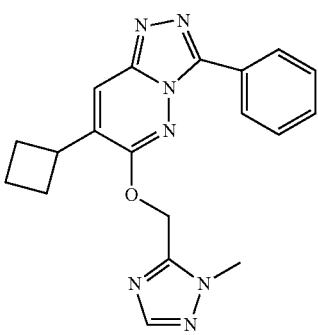
,
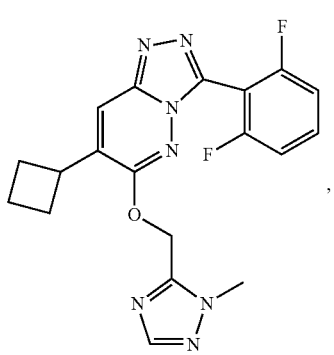
,
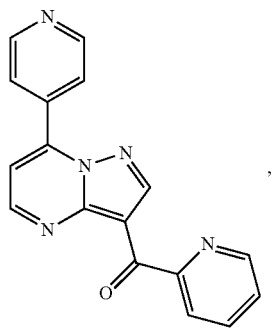
,
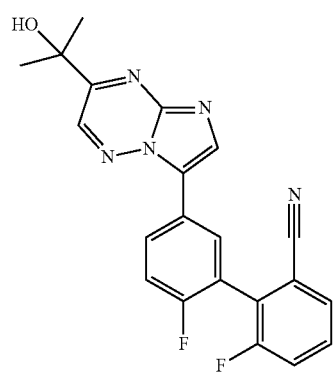
,
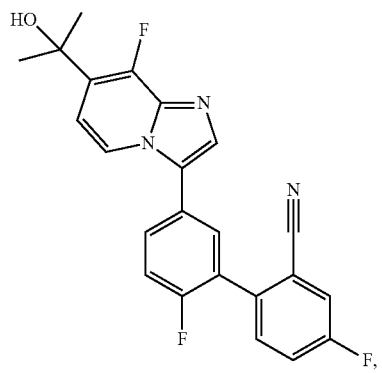
,
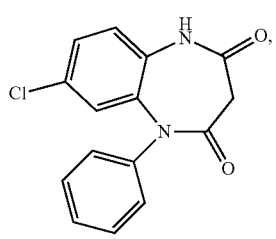
,
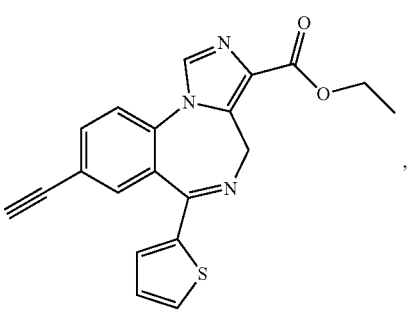
, 43
-continued

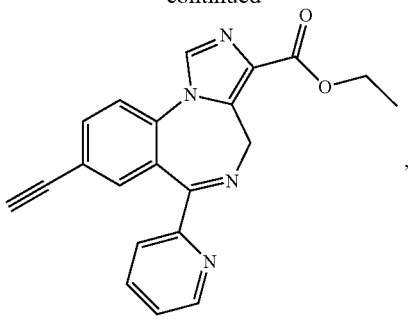

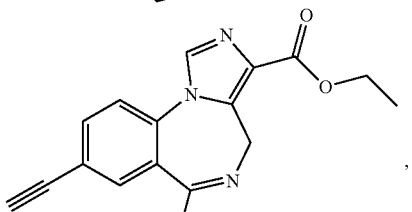

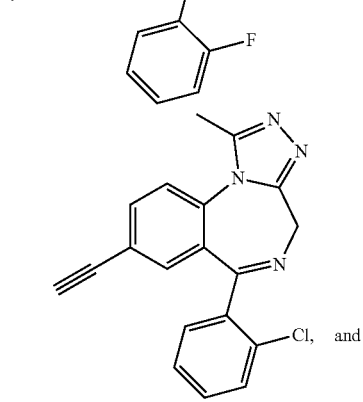

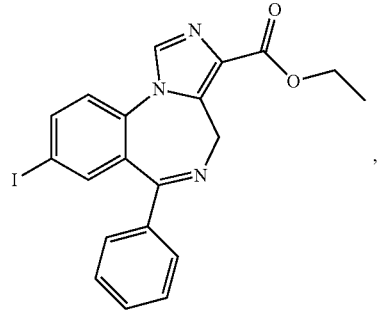

44 wherein the compound is in the form of a suspension in a saline solution, and wherein said pharmaceutical composition is formulated to provide a dose of at least 0.25 mg when administered to a subject.

6. The pharmaceutical composition of claim 5, wherein the suspension comprises polysorbate 80.

7. The pharmaceutical composition of claim 5, wherein the compound is:

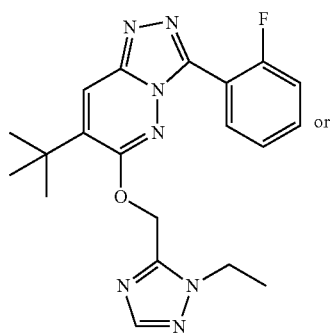

or

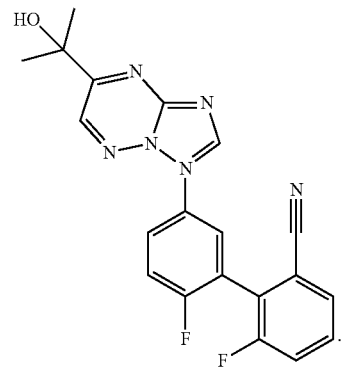

* * * * *

UNITED STATES PATENT AND TRADEMARK OFFICE
CERTIFICATE OF CORRECTION

PATENT NO. : 10,786,513 B2  
APPLICATION NO. : 16/045193  
DATED : September 29, 2020  
INVENTOR(S) : Zeilhofer et al.

Page 1 of 1

It is certified that error appears in the above-identified patent and that said Letters Patent is hereby corrected as shown below:

In the Claims

In Column 44, Line 38, Claim 7, The structure of the 2nd compound is incorrectly shown as:

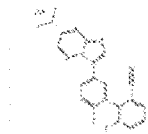

Should be shown as:

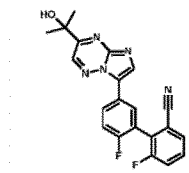

Signed and Sealed this  
Sixteenth Day of March, 2021

Drew Hirshfeld  
*Performing the Functions and Duties of the  
Under Secretary of Commerce for Intellectual Property and  
Director of the United States Patent and Trademark Office*